United States Patent
Staffler et al.

(10) Patent No.: US 10,576,131 B2
(45) Date of Patent: Mar. 3, 2020

(54) IL-23-P19 VACCINES

(71) Applicant: AFFIRIS AG, Vienna (AT)

(72) Inventors: Guenther Staffler, Vienna (AT); Dorian Winter, Vienna (AT)

(73) Assignee: AFFIRIS AG, Vienna (AT)

( * ) Notice: Subject to any disclaimer, the term of this patent is extended or adjusted under 35 U.S.C. 154(b) by 19 days.

(21) Appl. No.: 15/569,303

(22) PCT Filed: Jun. 3, 2016

(86) PCT No.: PCT/EP2016/062579
§ 371 (c)(1),
(2) Date: Oct. 25, 2017

(87) PCT Pub. No.: WO2016/193405
PCT Pub. Date: Dec. 8, 2016

(65) Prior Publication Data
US 2018/0110846 A1    Apr. 26, 2018

(30) Foreign Application Priority Data
Jun. 3, 2015  (EP) ..................................... 15170485

(51) Int. Cl.
| C07K 14/54 | (2006.01) |
| C07K 7/06 | (2006.01) |
| C07K 7/08 | (2006.01) |
| C07K 9/00 | (2006.01) |
| C07K 17/00 | (2006.01) |
| A61K 38/08 | (2019.01) |
| A61K 38/10 | (2006.01) |
| A61K 38/20 | (2006.01) |
| A61K 39/00 | (2006.01) |
| A61K 38/16 | (2006.01) |
| A61P 37/00 | (2006.01) |

(52) U.S. Cl.
CPC .......... *A61K 39/0008* (2013.01); *A61K 38/08* (2013.01); *A61K 38/10* (2013.01); *A61K 38/164* (2013.01); *A61K 38/20* (2013.01); *A61K 39/0005* (2013.01); *A61P 37/00* (2018.01); *C07K 7/06* (2013.01); *C07K 7/08* (2013.01); *C07K 9/00* (2013.01); *C07K 14/54* (2013.01); *C07K 17/00* (2013.01); *A61K 2039/6037* (2013.01); *A61K 2039/6081* (2013.01)

(58) Field of Classification Search
None
See application file for complete search history.

(56) References Cited

U.S. PATENT DOCUMENTS

| 2007/0048315 A1 | 3/2007 | Presta |
| 2009/0156788 A1 | 6/2009 | Presta et al. |
| 2011/0002942 A1 | 1/2011 | Presta et al. |

FOREIGN PATENT DOCUMENTS

| WO | WO 2005/108425 A1 | 11/2005 |
| WO | WO 2007/027714 A2 | 3/2007 |

OTHER PUBLICATIONS

Ratsimandresy et al, Vaccine 29; 2011; pp. 9329-9336.*
Guan et al, Immunotherapy; 2013; vol. 5; No. 12, pp. 1313-1322.*
Masakatsu Fukuda, et al., "IL-23 promotes growth and proliferation in human squamous cell carcinoma of the oral cavity", International Journal of Oncology, 36, 2010, pp. 1355-1365.
Oya Cingoz, "Ustekinumab", Mini-Review, Department of Molecular Biology and Microbiology, vol. 1, Issue 3, 2009, 6 pages.
Rui-Xue Leng, et al., "IL-23: A Promising Therapeutic Target for Systemic Lupus Erythematosus", Opinion, Archives of Medical Research, 41, 2010, pp. 221-225.
Wei Chi, et al., "Upregulated IL-23 and IL-17 in Behcet Patients with Active Uveitis", Investigative Ophthalmology & Visual Science, Association for Research in Vision and Ophthalmology, Jul. 2008, vol. 49, No. 7, pp. 3058-3064.
Guan et al., "Employing an IL-23 p19 vaccine to block IL-23 ameliorates chronic murine colitis", Research Article, XP008178305, Immunotherapy, 2013, 5(12), pp. 1313-1322.

(Continued)

*Primary Examiner* — Bridget E Bunner
*Assistant Examiner* — Fozia Hamud
(74) *Attorney, Agent, or Firm* — Oblon, McClelland, Maier & Neustadt, L.L.P.

(57) ABSTRACT

Disclosed is a vaccine, preferably for use in the prevention or treatment of an interleukin 23 (IL-23) related disease, that includes a peptide bound to a pharmaceutically acceptable carrier, wherein the peptide is QPEGHHWETQQIPSLS (SEQ ID No. 103; p8322), GHHWETQQIPSLSPSQP-WQRL QPEGHHWETQ (SEQ ID No. 98; p8461), TQQ-IPSLSPSQ (SEQ ID No. 99; p8400), QPEGHHWETQQ-IPSLSPSQ (SEQ ID No. 100; p9269), QPEGHHWETQQIPSLSPS (SEQ ID No. 101; p9269-C1), or QPEGHHWETQQIPSLSP (SEQ ID No. 102; p9269-C2), especially QPEGHHWETQQIPSLS (SEQ ID No. 103; p8322) and wherein the IL-23 related disease is one or more of psoriasis, psoriatic arthritis, rheumatoid arthritis, systemic lupus erythematosus, diabetes, preferably type 1 diabetes, atherosclerosis, inflammatory bowel disease (IBD)/M. Crohn, multiple sclerosis, Behcet disease, ankylosing spondylitis, Vogt-Koyanagi-Harada disease, chronic granulomatous disease, hidratenitis suppurtiva, anti-neutrophil cytoplasmic antibodies (ANCA-) associated vasculitides, neurodegenerative diseases, preferably M. Alzheimer or multiple sclerosis, atopic dermatitis, graft-versus-host disease, cancer, preferably Oesophagal carcinoma colorectal carcinoma, lung adenocarcinoma, small cell carcinoma, and squamous cell carcinoma of the oral cavity, especially psoriasis, neurodegenerative diseases or IBD.

13 Claims, 10 Drawing Sheets
Specification includes a Sequence Listing.

(56) References Cited

OTHER PUBLICATIONS

Sudeepta Aggarwal, Interleukin-23 Promotes a Distinct CD4 T Cell Activation State Characterized by the Production of Interleukin-17, The Journal of Biological Chemistry, vol. 278, No. 3,Issue of Jan. 17, 2003, pp. 1910-1914.
Tsuyoshi Uchida, et al., "Diphtheria Toxin and Related Proteins", The Journal of Biological Chemistry, vol. 248, No. 11, Issue of Jun. 10, 1973, pp. 3838-3844.
Rojo Anthony Ratsimandresy, et al., "Active Immunization against IL-23p19 improves experimental arthritis", Vaccine, 29, 2011, pp. 9329-9336.
K. Wippel-Slupetzky, et al., "Future Perspectives in the Treatment of Psoriasis", Management of Psoriasis, vol. 38, 2009, pp. 172-189.
Anders Sjölander, et al., "ISCOMs: an adjuvant with multiple functions", Journal of Leukocyte Biology, vol. 64. No. 6, 1998, pp. 713-723 (cover page).
Ling Zeng, M.D., et al., "Ankylosing spondylitis macrophages produce greater interleukin-23 in response to lipopolysaccharide without significant Unfolded Protein Response induction", NIH Public Access Author Manuscript, Arthritis Rheum., 2011, 63(12, 18 pages.

\* cited by examiner

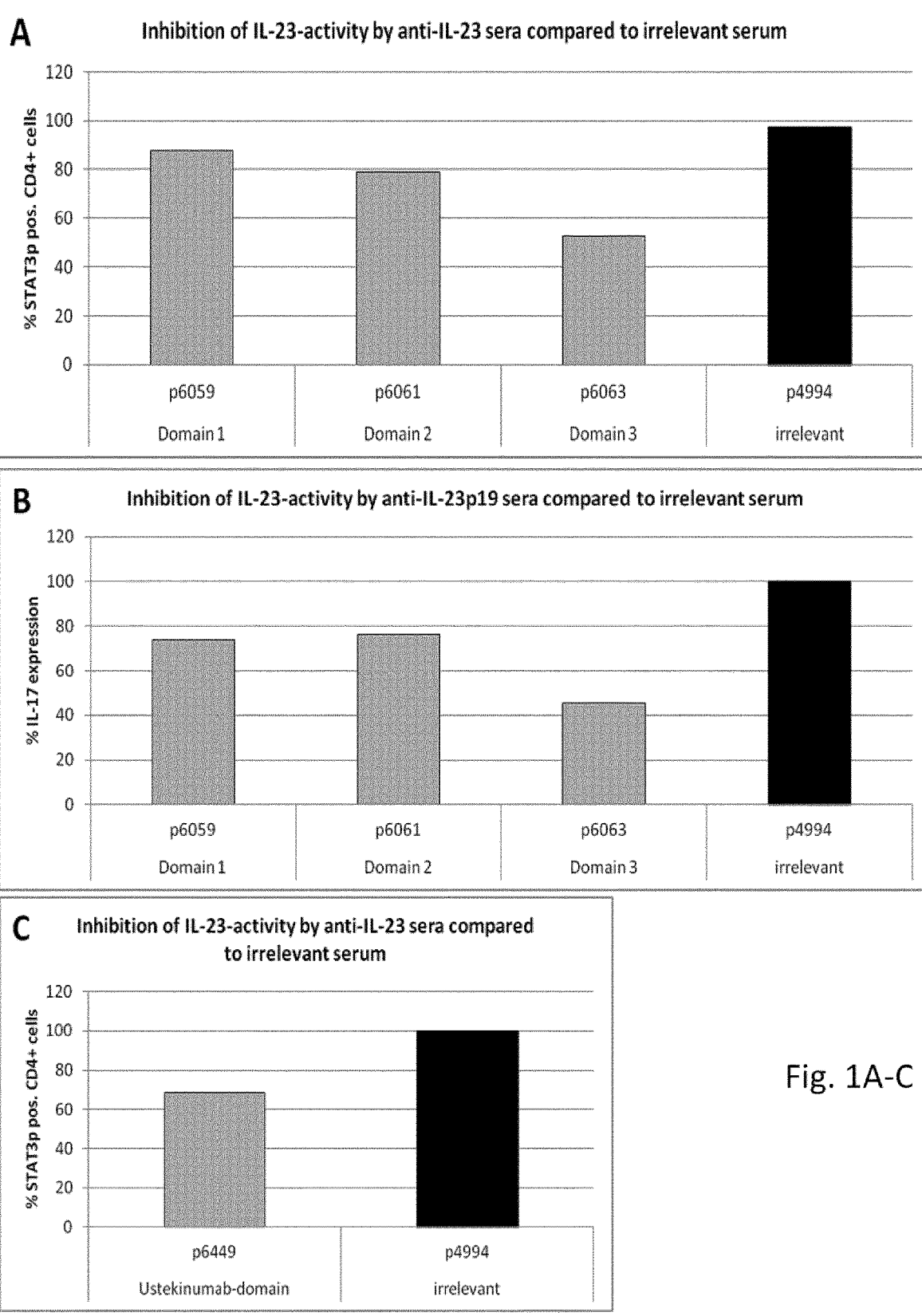
Fig. 1A-C

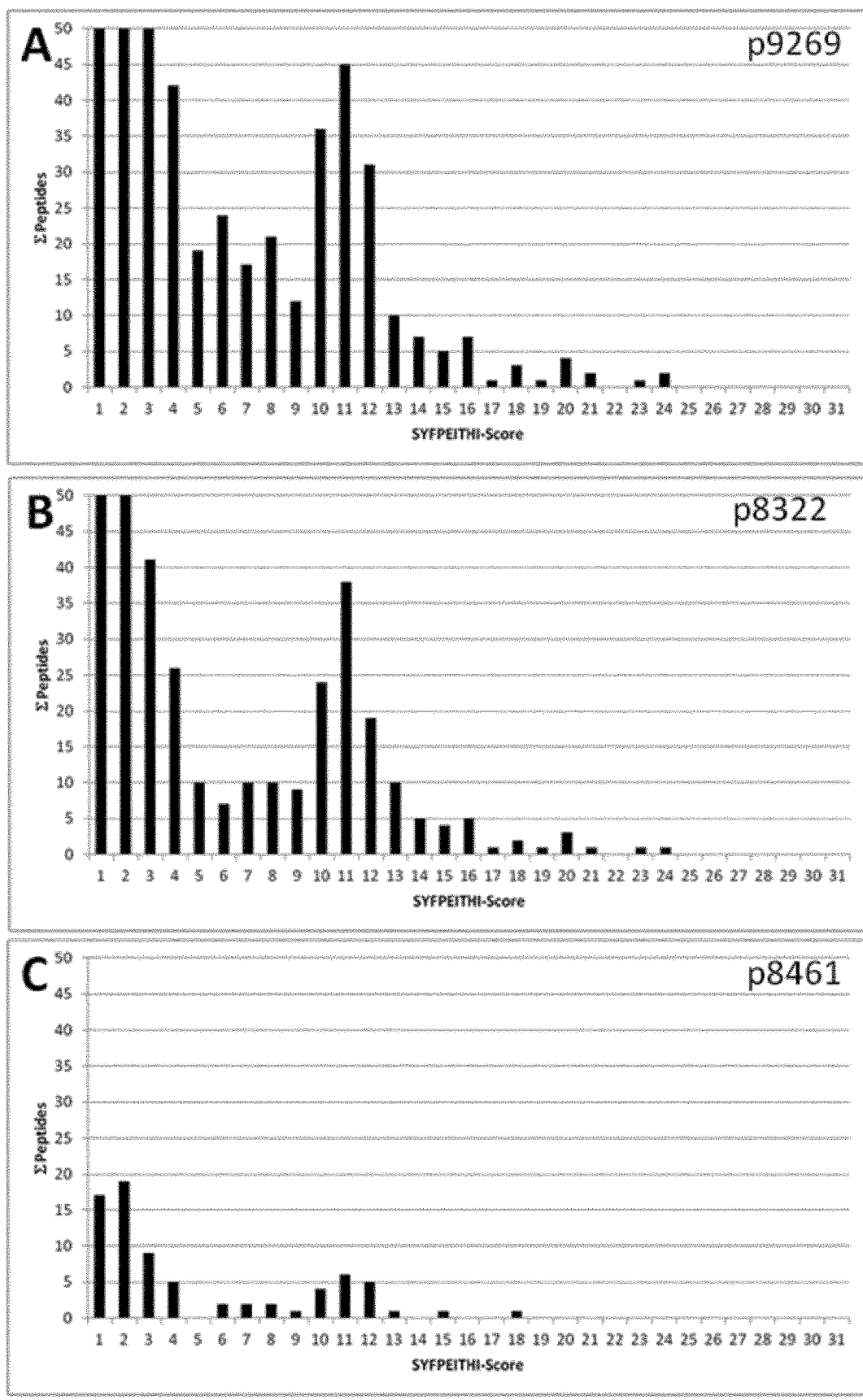
Fig. 6A-C

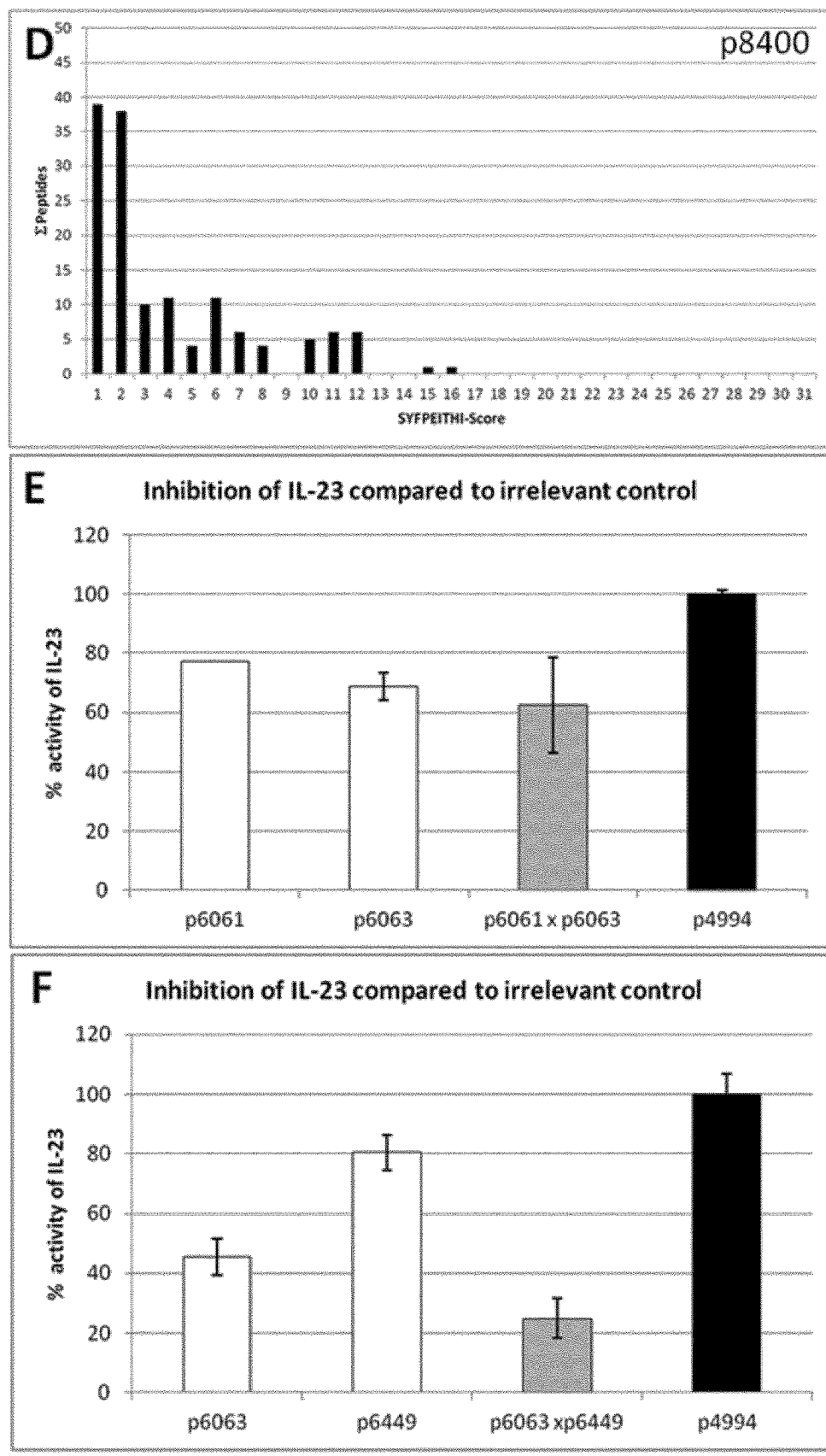
Fig. 6D-F

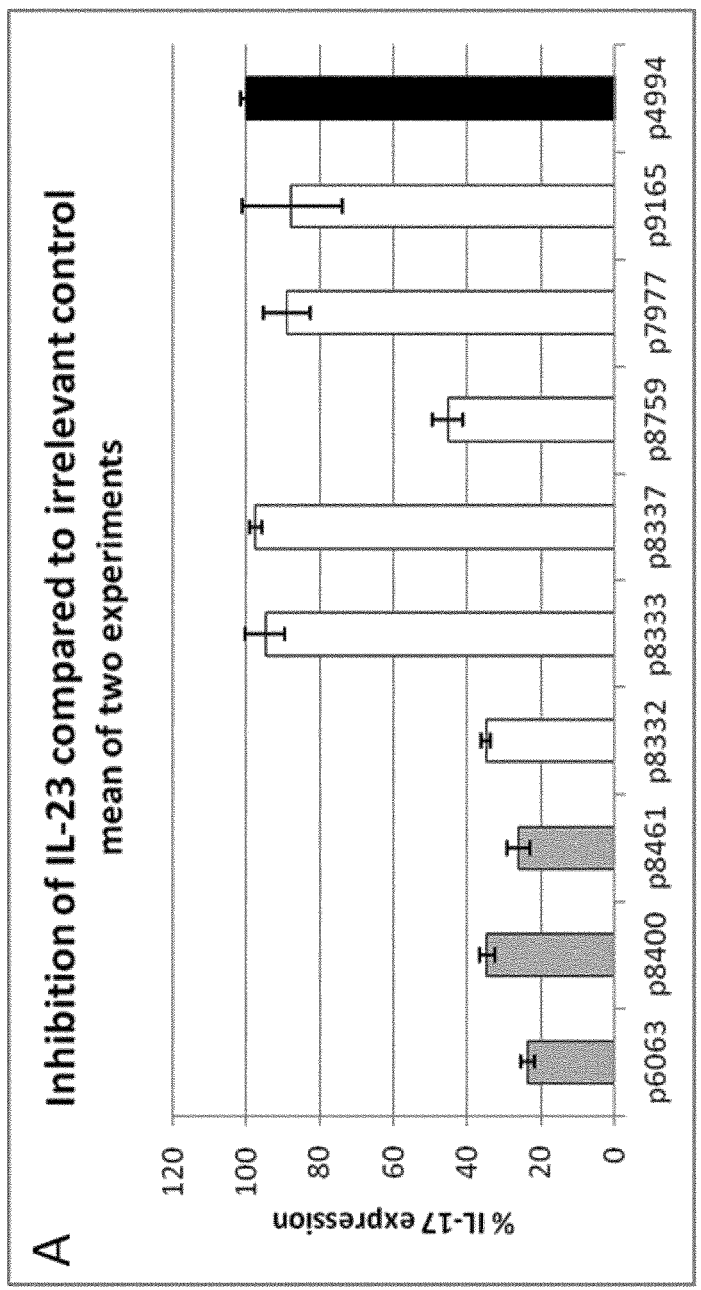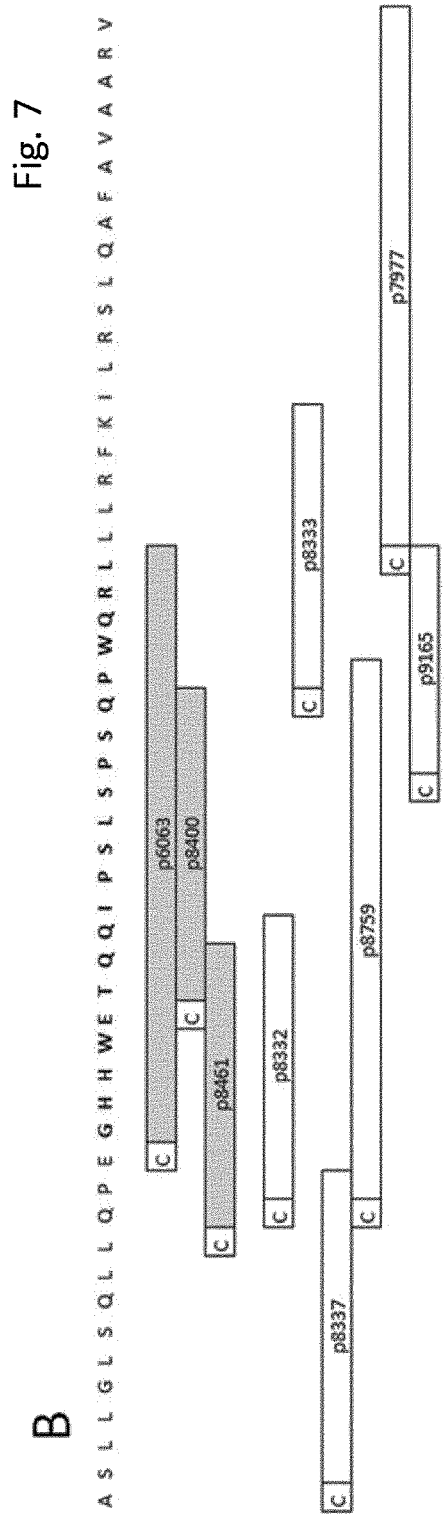
Fig. 7

IL-23-P19 VACCINES

CROSS-REFERENCE TO RELATED APPLICATIONS

This application is a national stage of PCT/EP2016/062579 filed Jun. 3, 2016 and claims the benefit of EP 15170485.5 filed Jun. 3, 2015.

FIELD OF THE INVENTION

The present invention relates to the prevention or treatment of interleukin 23 (IL-23) related diseases.

BACKGROUND OF THE INVENTION

IL-23 belongs to the IL-12-family and as such is a heterodimeric cytokine. It is composed of a p40-subunit—shared with IL-12, where it binds to a p35 entity—and a p19-subunit linked by a disulfide bond (Oppmann et al., 2000). When first discovered, the p19 subunit was designated IL-B30. It was soon discovered that this subunit displays biological functions only when paired with the p40 subunit (Oppmann et al., 2000).

Several functional domains have been described in the subunits: A domain forming the interaction-surface of p19 with its receptor IL23R, a domain forming the interaction surface of p40 with a part of the IL-12 receptor, IL12Rβ1, a domain for the interaction of p40 with IL23R and domains on both p19 and p40, facilitating interaction of the two subunits.

The receptor conferring specificity for IL-23 is a member of the hemopoietin receptor family and is paired with IL-12Rβ1, the receptor binding IL12p40. When bound by its ligand, the receptor signals through the JAK/STAT-pathway, involving predominantly STAT3, but also STAT1, STAT4, and STAT5.

Functionally, IL-23 is involved in the induction of proliferation of memory T cells (Oppmann et al., 2000) and is unique in the generation, stabilization and maintainance of Th17 cells from naïve T cells. Th17 cells are a recently described line of T cell differentiation apart from Th1 and Th2 cells, and express a large number of cytokines and proinflammatory effectors. Furthermore, IL-23 plays a role in the biology of various Type 17 immune cells, a polymorphous group of cell populations with mostly yet unclear properties and roles (Gaffen et al., 2014).

Tests for IL-23-function are sparse. The standard assay today is a cellular assay, which quantifies the ability of isolated murine splenocytes to produce IL-17A after stimulation with human IL-23 (Aggarwal et al., 2003). This assay is routinely used by manufacturers of rIL-23 to assess the quality of their products. A molecular assay, termed "STAT3-Assay" capitalizes on the fact that STAT3 is phosphorylated at Y705 following binding of IL-23 to its receptor and signalling through JAK2 and TYK2. Phosphorylation of STAT3 can be monitored with STAT3p-specific monoclonal antibodies in flow cytometry. Other assays based on colorimetric reactions after IL-23-induced cell growth of different cell lines have been reported in the literature but failed to be reproducible in our hands.

IL-23 has been shown to be significantly involved in several malignancies. Most prominent among these and best researched in this context stands psoriasis.

Psoriasis is a chronic and recurrent inflammatory dermatosis that can be triggered by exogenous and endogenous noxes (reviewed in (Wippel-Slupetzky and Stingl, 2009)). The disease affects approximately 2% of the population and is associated to a decreased quality of life (discomfort, disability, curtailed social interaction, comorbidities). As the disease is still incurable, treatment-intensive and a massive strain to patients in physic, psychic, social and material aspects, which can amount to suicidal tendencies, there is an ample need for novel and effective therapies. The yearly market for psoriasis-related therapies is estimated at 3.3 billion USD/year.

The etiology of the disease remains unresolved, numerous possible endo- and exogenous triggers concur with a genetic predisposition, the inheritance patterns for susceptibility to psoriasis being complex. Recent data show that IL-23 plays a central role in the development and perpetuation of the disease. Both the cytokine and its receptor are genetically associated to the malady, and the cytokines' expression is clearly increased in psoriatic lesions as compared to normal skin (Lee et al., 2004).

IL-23, a large proportion of which is produced by monocytes and dendritic cells—probably triggered by products of damaged keratinocytes—contributes to inflammation by stimulating and maintaining Th17 cells, which in turn express several cytokines, among them IL-17A that activates production of various inflammatory effectors and chemokines and thus contributes to the creation of an inflammatory environment, and IL-22, which triggers hyperproliferation of keratinocytes. The damaged keratinocytes in turn attract chemotactically more cells of the immune system, causing aggravation of the inflammation (Nestle et al., 2009).

Besides psoriasis, several other diseases have been linked to a deregulation of the Th17/IL-23 pathway (reviewed e.g. in (Gaffen et al., 2014)), e.g.: Rheumatoid arthritis, systemic lupus erythematosus, Diabetes, Atherosclerosis, inflammatory bowel disease/M. Crohn, multiple sclerosis, Behçet disease, ankylosing spondylitis, Vogt-Koyanagi-Harada disease, chronic granulomatous disease, hidratenitis suppurtiva, ANCA-associated vasculitides and M. Alzheimer, as well as various forms of cancer. The list is growing at a fast pace.

Novel antibody-based therapies aim at a reduction of IL-23 in patients with psoriasis. Clinical studies demonstrate that repeated application of antibodies that interfere with the binding of IL-23 to its receptors lead to a significant and enduring improvement of the diseases' symptoms (Cingoz, 2009). As a consequence of these studies, one antibody (Ustekinumab/Stelara®) has been approved for the treatment of psoriasis, while several others are in development. Vaccination of mice with certain KLH-coupled peptides derived from the murine IL-23 subunit-sequences has been demonstrated to be effective against arthritis and IBD.

WO 2005/108425 A1 relates to the IL-23p19 antigen in array form. The article of Ratsimandresy et al. (Vaccine 29 (2011): 9329-9336) reports an active immunization against IL-23p19 using specific peptides. The article of Guan et al. (Immunotherapy 5 (2013): 1313-1322) discloses an IL-23p19 vaccine to block IL-23 ameliorating chronic murine colitis. WO 2007/027714 A2 discloses engineeres anti-IL-23-antibodies.

SUMMARY OF THE INVENTION

It is an object of the present invention to provide alternative and/or improved means for combatting IL-23 related diseases, especially psoriasis. These means should preferably allow an efficient and cost-effective prevention and treatment regime for such diseases without significant adverse reactions to the patients treated. Moreover, such means should preferably allow prevention and treatment of high patient numbers in a reliable manner and be easily accessible to and adaptable in public and private health care systems.

Therefore, the present invention discloses a vaccine for use in the prevention or treatment of an interleukin 23 (IL-23) related disease, comprising a peptide bound to a pharmaceutically acceptable carrier, wherein said peptide is selected from the group QPEGHHWETQQIPSLS (SEQ ID No. 103; p8322), QPEGHHWETQ (SEQ ID No. 98; p8461), TQQIPSLSPSQ (SEQ ID No. 99; p8400), QPEGHHWETQQIPSLSPSQ (SEQ ID No. 100; p9269), QPEGHHWETQQIPSLSPS (SEQ ID No. 101; p9440), and QPEGHHWETQQIPSLSP (SEQ ID No. 102; p9441), especially QPEGHHWETQQIPSLS (SEQ ID No. 103; p8322) and wherein said IL-23 related disease is selected from the group psoriasis, psoriatic arthritis, rheumatoid arthritis, systemic lupus erythematosus, diabetes, preferably type 1 diabetes; atherosclerosis, inflammatory bowel disease (IBD)/M. Crohn, multiple sclerosis, Behçet disease, ankylosing spondylitis, Vogt-Koyanagi-Harada disease, chronic granulomatous disease, hidratenitis suppurtiva, anti-neutrophil cytoplasmic antibodies (ANCA-) associated vasculitides, neurodegenerative diseases, preferably M. Alzheimer or multiple sclerosis; atopic dermatitis, graft-versus-host disease, cancer, preferably oesophagal carcinoma, colorectal carcinoma, lung adenocarcinoma, small cell carcinoma, or squamous cell carcinoma of the oral cavity; preferably psoriasis, psoriatic arthritis, neurodegenerative diseases, especially M. Alzheimer, diabetes, especially type 1 diabetes, atherosclerosis, or IBD; especially psoriasis, psoriatic arthritis, or IBD.

DETAILED DESCRIPTION OF THE INVENTION

With the present invention, well defined peptides, termed AFFITOPEs®, are provided which can be used as vaccinating agents for the onset, mitigation or cure of psoriasis and/or other human diseases that are caused or exacerbated by a dysregulation of the Th17/IL-23 pathway. Such diseases are well described in the art, for example by Leng et al. (systemic lupus erythematosus), Monteleone et al. (IBD/M. Crohn), Brennan et al. (rheumatoid arthritis), Chi et al. 2008 (Behçet disease), Zeng et al. (ankylosing spondylitis (M. Bechterev)), Chi et al. 2007 (Vogt-Koyanagi-Harada disease), Schlapbach et al. (hidradenitis suppurativa), Fukuda et al. (cancer, such as squamous cell carcinoma, non small cell lung cancer), or vom Berg et al. (M. Alzheimer).

Furthermore, the IL-23-directed vaccines can be used together with vaccines against other targets, as recent data suggest that IL-23-driven inflammation can exacerbate other diseases, such as Alzheimer's disease or possibly diabetes. The antibodies elicited by the AFFITOPEs® according to the present invention are specifically directed against IL-23, the cytokine that plays a crucial role at an early point of the pathway. The advantage of an active immunization over passive vaccination with monoclonal antibodies lies in the lower cost for the individual and/or the health care system, the presumably longer duration of the immune response after completion of the regimen and the lower probability for the elicitation of anti-drug-antibodies due to the polyclonal nature of the response.

The vaccine according to the present invention is composed of a IL-23-specific AFFITOPE® (the "peptides according to the present invention") bound to a pharmaceutically acceptable carrier. This carrier can be directly coupled to the peptides according to the present invention. It is also possible to provide certain linker molecules between the peptide and the carrier. Provision of such linkers may result in beneficial properties of the vaccine, e.g. improved immunogenicity, improved specificity or improved handling (e.g. due to improved solubility or formulation capacities). According to a preferred embodiment, the peptides according to the present invention contain at least one cysteine residue bound to the N- or C-terminus of the peptide. Specifically preferred examples are the peptides according to SEQ ID Nos. 16 (CGHHWETQQIPSLSPSQP-WQRL; p6063), 28 (CQPEGHHWETQ; p8461), 33 (CTQQIPSLSPSQ; p8400), 43 (CQPEGHHWETQQIPSLSPSQ; p9269), 46 (CQPEGHHWETQQIPSLSPS; p9440), 47 (CQPEGHHWETQQIPSLSP; p9441), and 24 (CQPEGHHWETQQIPSLS; p8322). This cysteine residue can then be used to covalently couple the peptide to the carrier. Although it is possible to provide the cysteine residue at any appropriate location of the peptide, coupling the cysteine residue to the N-terminus of the peptide is specifically preferred.

Accordingly, in a preferred vaccine according to the present invention the peptide is bound to the carrier by a linker, preferably a peptide linker, especially a peptide linker having from 2 to 5 amino acid residues. Preferred linkers are those that have been applied and/or approved in vaccine technology; peptide linkers comprising or consisting of Cysteine residues, such as Gly-Gly-Cys, Gly-Cys, Cys-Gly and Cys-Gly-Gly, are specifically preferred.

According to a preferred embodiment, the vaccine according to the present invention is a biepitopic vaccine, especially a vaccine comprising a peptide of the group QPEGHHWETQQIPSLSPSQ (SEQ ID No. 100; p9269), QPEGHHWETQQIPSLSPS (SEQ ID No. 101; p9440), QPEGHHWETQQIPSLSP (SEQ ID No. 102; p9441), and QPEGHHWETQQIPSLS (SEQ ID No. 103; p8322). Biepitopic vaccines contain longer peptides combining two epitopes. Possible scenarios include naturally occurring stretches of epitopes in either their original or altered sequence, or the combination of epitopes from distant locations on the same or even different subunits of the complex, joined in one peptide, possibly separated by a spacer. According to a preferred embodiment, these biepitopic peptides are combined with other target peptides, preferably with further IL23p40 and/or IL23p19 peptides, such as one or more peptides according to SEQ ID Nos. 116-134 (see below), especially peptide p6449 (p40$_{35-49}$) and/or peptide p6061 (p19$_{100-119}$).

According to a further preferred embodiment, the vaccine according to the present invention is a binary vaccine, especially a vaccine comprising a peptide from the group QPEGHHWETQQIPS (SEQ ID No. 104; p8459), QPEGHHWETQQIP (SEQ ID No. 105; p8459-1), QPEGHHWETQQI (SEQ ID No. 106; p8460), QPEGHHWETQQ (SEQ ID No. 107; p8460-1), QPEGHHWETQ (SEQ ID No. 98; p8461), QPEGHHWET (SEQ ID No. 108, p8461-1), QPEGHHWE (SEQ ID No. 109; p8462) and a peptide from the group TQQIPSLSPSQPWQ (SEQ ID No. 110, p8397), TQQIPSLSPSQPW (SEQ ID No. 111, p8398), TQQIPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), TQQIPSLS (SEQ ID No 115; p8763), preferably the peptide QPEGHHWETQ (SEQ ID No. 98; p8461) and the peptide TQQIPSLSPSQ (SEQ ID No. 99; p8400), each bound to a separate carrier. In binary vaccines, two monoepitopic peptides are concomitantly applied to the subject. Possible scenarios involve peptides from the same domain, from spatially distinct domains from different subunits of a molecule/complex or even from different targets. Peptides can be coupled to the same or to different carriers, the latter to avoid carrier-dependent epitope inhibition. Such binary vaccines may either be included in one vaccine (as a vaccine with multiple specificity) of be provided in a kit comprising one or more vaccines. Although modern vaccination strategies prefer usage of vaccines with multiple specificity (which is also preferred according to the present invention), there may be strategies, especially when dealing with addressing a complex pathway, such as the Th17/IL-23 pathway, wherein multiple vaccines, each with different specificity) are applied instead of vaccines with multiple specificities. Accordingly, the present invention also provides a vaccine kit comprising a vaccine according to the present invention and a further vaccine against a disease-related protein, preferably addressing a target particular to the Th17/IL-23 pathway, preferably an anti-IL-23 vaccine such as the IL12/23p40-derived peptide p6449 (p40$_{35-49}$), especially an anti-IL-23p19 vaccine such as the peptide p6061 (p19$_{100-119}$).

In WO 2005/108425 A1 [Bachman/Cytos], FYEKLLGS-DIFTGE (SEQ ID No. 116), FYEKLLGSDIFTGEPSLL-PDSP (SEQ ID No. 117), VAQLHASLLGLSQLLQP (SEQ ID No. 118), GEPSLLPDSPVAQLHASLLGLSQLLQP (SEQ ID No. 119), PEGHHWETQQIPSLSPSQP (SEQ ID No. 120;=p8759), PSLLPDSP (SEQ ID No. 121), LPD-SPVA (SEQ ID No. 122), FYEKLLGSDIFTGEPSLLPD-SPVAQLHASLLGLSQLLQP (SEQ ID No. 123), LLPDSP (SEQ ID No. 124), LLGSDIFTGEPSLLPDSPVAQL-HASLLG (SEQ ID No. 125), FYEKLLGSDIFTGEPSLL-PDSPVAQLHASLLG (SEQ ID No. 126), QPEGHHW (SEQ ID No. 127), LPDSPVGQLHASLLGLSQLLQ (SEQ ID No. 128) and QCQQLSQKLCTLAWSAHPLV (SEQ ID No. 129) derived from IL-23p19 were proposed as vaccination peptides for IL-23. In WO 03/084979 A2 [Zagury], GHMDLREEGDEETT (SEQ ID No. 130), LLPDSPVGQL-HASLLGLSQ (SEQ ID No. 131) and LLRFKIL-RSLQAFVAVAARV (SEQ ID No. 132;=p7977) from IL-23p19 and LLLHKKEDGIWSTDILKDQKEPKNKT-FLRCE (SEQ ID No. 133) and KSSRGSSDPQG (SEQ ID No. 134) from the IL-12/23 p40 subunit were mentioned as possible anti-cytokine vaccines. Vaccination against components of the Th17/IL-23 axis has been attempted in various animal models of Th17/IL-23-dependent diseases. Tested formulations were total murine IL-12 (Uyttenhove) and murine IL-17 (aa26-158) (Sondegger) coupled to carriers as well as the murine IL-12/23p40-derived peptides, PEEDDITWTSDQRHGVIGS (SEQ ID No. 135), PDSRAVTCGMASLSAEKV (SEQ ID No. 136) and TPDAPGETV (SEQ ID No. 137) recombinantly joined to HBcAg (Guan 2009, 2012). Furthermore, the murine IL-23p19-derived sequences DSDIFKGEPALLPDSP-MEQL (SEQ ID No. 138) and TQQMPSLSSSQQWQR-PLLRS (SEQ ID No. 139) have been investigated (Ratsimandresy). Accordingly, in a preferred embodiment of the present vaccine, the peptides according to the present invention may be combined with one or more of such prior art peptides, especially with one or more of the group of SEQ ID Nos. 116-134.

According to a further embodiment, the present invention also relates to the peptides according to the present invention as such or as provided in a pharmaceutical preparation, i.e. a peptide, selected from the group GHHWETQQIPSLSP-SQPWQRL (SEQ ID No. 97; p6063), QPEGHHWETQ (SEQ ID No. 98; p8461), TQQIPSLSPSQ (SEQ ID No. 99; p8400), QPEGHHWETQQIPSLSPSQ (SEQ ID No. 100; p9269), QPEGHHWETQQIPSLSPS (SEQ ID No. 101; p9440), QPEGHHWETQQIPSLSP (SEQ ID No. 102; p9441), QPEGHHWETQQIPSLS (SEQ ID No. 103; p8322), QPEGHHWETQQIPS (SEQ ID No. 104; p8495), QPEGHHWETQQIP (SEQ ID No. 105; p8459-1), QPEGH-HWETQQI (SEQ ID No. 106; p8460), QPEGHHWETQQ (SEQ ID No. 107; p8460-1), QPEGHHWETQ (SEQ ID No. 98; p8461), QPEGHHWET (SEQ ID No. 108, p8461-1), QPEGHHWE (SEQ ID No. 109; p8462) and a peptide from the group TQQIPSLSPSQPWQ (SEQ ID No. 110, p8397), TQQIPSLSPSQPW (SEQ ID No. 111, p8398), TQQ-IPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), and TQQ-IPSLS (SEQ ID No 115; p8763). Another aspect of the present invention relates to a peptide pair, wherein one peptide is selected from the group QPEGHHWETQQIPS (SEQ ID No. 104; p8495), QPEGHHWETQQIP (SEQ ID No. 105; p8459-1), QPEGHHWETQQI (SEQ ID No. 106; p8460), QPEGHHWETQQ (SEQ ID No. 107; p8460-1), QPEGHHWETQ (SEQ ID No. 98; p8461), QPEGHHWET (SEQ ID No. 108, p8461-1), QPEGHHWE (SEQ ID No. 109; p8462) and the second peptide is selected from the group TQQIPSLSPSQPWQ (SEQ ID No. 110, p8397), TQQIPSLSPSQPW (SEQ ID No. 111, p8398), TQQ-IPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), TQQIPSLS (SEQ ID No 115; p8763), preferably the peptide QPEGH-HWETQ (SEQ ID No. 98; p8461) and the peptide TQQ-IPSLSPSQ (SEQ ID No. 99; p8400). Besides the use of the present peptides (together with a carrier) for vaccination purposes, the present peptides or peptide pairs may be used for other purposes, preferably medical purposes, especially diagnostic purposes. For example, the present peptides may be used for observing the performance of the vaccination with the present vaccines and/or to capture, identify or bind to antibodies elicited against the present vaccines. For such purposes, the present peptides may be bound to surfaces (or pharmaceutically non-acceptable carriers) or to marker substances, such as magnetic, colour or colourigenic, radioactive or fluorescent markers.

According to the present invention, any suitable carrier molecule for carrying the present peptides may be used for the vaccines according to the present invention, as long as this carrier is pharmaceutically acceptable, i.e. as long as it is possible to provide such carrier in a pharmaceutical preparation to be administered to human recipients of such vaccines. Preferred carriers according to the present invention are protein carriers, especially keyhole limpet haemocyanin (KLH), tetanus toxoid (TT), Haemophilus influenzae protein D (protein D), or diphtheria toxin (DT). Preferred carriers are also non-toxic diphtheria toxin mutant, especially CRM 197, CRM 176, CRM 228, CRM 45, CRM 9, CRM 102, CRM 103 and CRM 107 (see e.g. Uchida et al J. Biol. Chem. 218; 3838-3844, 1973), whereby CRM 197 is particularly preferred.

The vaccine according to the present invention is a vaccine preparation or composition suitable to be applied to human individuals (in this connection, the terms "vaccine", "vaccine composition" and "vaccine preparation" are used interchangeably herein and identify a pharmaceutical preparation comprising a peptide according to the present invention bound to a pharmaceutically accepted carrier).

According to a preferred embodiment, the vaccine according to the present invention is formulated with an adjuvant, preferably wherein the peptide bound to the carrier is adsorbed to alum.

The vaccine according to the present invention is preferably formulated for intravenous, subcutaneous, intradermal or intramuscular administration, especially for subcutaneous or intradermal administration.

The vaccine composition according to the present invention preferably contains the peptide according to the present invention in an amount from 0.1 ng to 10 mg, preferably 10 ng to 1 mg, in particular 100 ng to 100 μg. The vaccines of the present invention may be administered by any suitable mode of application, e.g. i.d., i.v., i.p., i.m., intranasally, orally, subcutaneously, transdermally, intradermally etc. and in any suitable delivery device (O'Hagan et al., Nature Reviews, Drug Discovery 2 (9), (2003), 727-735). Therefore, the vaccine of the present invention is preferably formulated for intravenous, subcutaneous, intradermal or intramuscular administration (see e.g. "Handbook of Pharmaceutical Manufacturing Formulations", Sarfaraz Niazi, CRC Press Inc, 2004).

The vaccine according to the present invention comprises in a pharmaceutical composition the peptides according to the invention in an amount of from 0.1 ng to 10 mg, preferably 10 ng to 1 mg, in particular 100 ng to 100 μg, or, alternatively, e.g. 100 fmol to 10 μmol, preferably 10 pmol to 1 μmol, in particular 100 pmol to 100 nmol. Typically, the vaccine may also contain auxiliary substances, e.g. buffers, stabilizers etc.

Typically, the vaccine composition of the present invention may also comprise auxiliary substances, e.g. buffers, stabilizers etc. Preferably, such auxiliary substances, e.g. a pharmaceutically acceptable excipient, such as water, buffer and/or stabilizers, are contained in an amount of 0.1 to 99% (weight), more preferred 5 to 80% (weight), especially 10 to 70% (weight). Possible administration regimes include a weekly, biweekly, four-weekly (monthly) or bimonthly treatment for about 1 to 12 months; however, also 2 to 5, especially 3 to 4, initial vaccine administrations (in one or two months), followed by booster vaccinations 6 to 12 months thereafter or even years thereafter are preferred—besides other regimes already suggested for other vaccines.

According to a preferred embodiment of the present invention the peptide in the vaccine is administered to an individual in an amount of 0.1 ng to 10 mg, preferably of 0.5 to 500 μg, more preferably 1 to 100 μg, per immunization. In a preferred embodiment these amounts refer to all peptides present in the vaccine composition of the present invention. In another preferred embodiment these amounts refer to each single peptides present in the composition. It is of course possible to provide a vaccine in which the various different peptides are present in different or equal amounts. However, the peptides of the present invention may alternatively be administered to an individual in an amount of 0.1 ng to 10 mg, preferably 10 ng to 1 mg, in particular 100 ng to 300 μg/kg body weight (as a single dosage).

The amount of peptides that may be combined with the carrier materials to produce a single dosage form will vary depending upon the host treated and the particular mode of administration. The dose of the composition may vary according to factors such as the disease state, age, sex and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the vaccines of the present invention may be administered to an individual at intervals of several days, one or two weeks or even months or years depending always on the level of antibodies induced by the administration of the composition of the present invention.

In a preferred embodiment of the present invention the vaccine composition is applied between 2 and 10, preferably between 2 and 7, even more preferably up to 5 and most preferably up to 4 times. This number of immunizations may lead to a basic immunization. In a particularly preferred embodiment the time interval between the subsequent vaccinations is chosen to be between 2 weeks and 5 years, preferably between 1 month and up to 3 years, more preferably between 2 months and 1.5 years. An exemplified vaccination schedule may comprise 3 to 4 initial vaccinations over a period of 6 to 8 weeks and up to 6 months. Thereafter the vaccination may be repeated every two to ten years. The repeated administration of the vaccines of the present invention may maximize the final effect of a therapeutic vaccination.

According to a preferred embodiment of the present invention the vaccine is formulated with at least one adjuvant.

"Adjuvants" are compounds or a mixture that enhance the immune response to an antigen (i.e. the AFFITOPE®s according to the present invention). Adjuvants may act primarily as a delivery system, primarily as an immune modulator or have strong features of both. Suitable adjuvants include those suitable for use in mammals, including humans.

According to a particular preferred embodiment of the present invention the at least one adjuvant used in the vaccine composition as defined herein is capable to stimulate the innate immune system.

Innate immune responses are mediated by toll-like receptors (TLR's) at cell surfaces and by Nod-LRR proteins (NLR) intracellularly and are mediated by D1 and D0 regions respectively. The innate immune response includes cytokine production in response to TLR activation and activation of Caspase-1 and IL-1β secretion in response to certain NLRs (including Ipaf). This response is independent of specific antigens, but can act as an adjuvant to an adaptive immune response that is antigen specific.

A number of different TLRs have been characterized. These TLRs bind and become activated by different ligands, which in turn are located on different organisms or structures. The development of immunopotentiator compounds that are capable of eliciting responses in specific TLRs is of interest in the art. For example, U.S. Pat. No. 4,666,886 describes certain lipopeptide molecules that are TLR2 agonists. WO 2009/118296, WO 2008/005555, WO 2009/111337 and WO 2009/067081 each describe classes of small molecule agonists of TLR7. WO 2007/040840 and WO 2010/014913 describe TLR7 and TLR8 agonists for treatment of diseases. These various compounds include small molecule immunopotentiators (SMIPs).

The at least one adjuvant capable to stimulate the innate immune system preferably comprises or consists of a Toll-like receptor (TLR) agonist, preferably a TLR1, TLR2, TLR3, TLR4, TLR5, TLR7, TLR8 or TLR9 agonist, particularly preferred a TLR4 agonist.

Agonists of Toll-like receptors are well known in the art. For instance a TLR 2 agonist is Pam3CysSerLys4, peptidoglycan (Ppg), PamCys, a TLR3 agonist is IPH 31XX, a TLR4 agonist is an Aminoalkyl glucosaminide phosphate, E6020, CRX-527, CRX-601, CRX-675, 5D24.D4, RC-527, a TLR7 agonist is Imiquimod, 3M-003, Aldara, 852A, R850, R848, CL097, a TLR8 agonist is 3M-002, a TLR9 agonist is Flagellin, Vaxlmmune, CpG ODN (AVE0675, HYB2093), CYT005-15 AllQbG10, dSLIM.

According to a preferred embodiment of the present invention the TLR agonist is selected from the group consisting of monophosphoryl lipid A (MPL), 3-de-O-acylated monophosphoryl lipid A (3D-MPL), poly I:C, GLA, flagellin, R848, imiquimod and CpG.

The composition of the present invention may comprise MPL. MPL may be synthetically produced MPL or MPL obtainable from natural sources. Of course it is also possible to add to the composition of the present invention chemically modified MPL. Examples of such MPL's are known in the art.

According to a further preferred embodiment of the present invention the at least one adjuvant comprises or consists of a saponin, preferably QS21, a water in oil emulsion and a liposome.

The at least one adjuvant is preferably selected from the group consisting of MF59, AS01, AS02, AS03, AS04, aluminium hydroxide and aluminium phosphate.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

Examples of known suitable immune modulatory type adjuvants that can be used in humans include, but are not limited to saponins extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, and the like.

Examples of known suitable immune modulatory type adjuvants with both delivery and immune modulatory features that can be used in humans include, but are not limited to ISCOMS (see, e.g., Sjölander et al. (1998) J. Leukocyte Biol. 64:713; WO90/03184, WO96/11711, WO 00/48630, WO98/36772, WO00/41720, WO06/134423 and WO07/026,190) or GLA-EM which is a combination of a Toll-like receptor agonists such as a TLR4 agonist and an oil-in-water emulsion.

Further exemplary adjuvants to enhance effectiveness of the vaccine compositions of the present invention include, but are not limited to: (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) (see e.g., GB-2220221, EP-A-0689454), optionally in the substantial absence of alum when used with pneumococcal saccharides (see e.g. WO00/56358); (6) combinations of 3dMPL with, for example, QS21 and/or oil-in-water emulsions (see e.g. EP-A-0835318, EP-A-0735898, EP-A-0761231); (7) a polyoxyethylene ether or a polyoxyethylene ester (see e.g. WO99/52549); (8) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (9) a saponin and an immunostimulatory oligonucleotide (e.g. a CpG oligonucleotide) (WO 00/62800); (10) an immunostimulant and a particle of metal salt (see e.g. WO00/23105); (11) a saponin and an oil-in-water emulsion e.g. WO99/11241; (12) a saponin (e.g. QS21)+3dMPL+IM2 (optionally+a sterol) e.g. WO98/57659; (13) other substances that act as immunostimulating agents to enhance the efficacy of the composition. Muramyl peptides include N-acetyl-muramyl-L-threonyl-D-isoglutamine (thr-MDP), N-25 acetyl-normnuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Particularly preferred compositions of the present invention comprise as adjuvant an oil-in-water emulsion with or without Toll-like receptor agonists, as well as liposomes and/or saponin-containing adjuvants, with or without Toll-like receptor agonists. The composition of the present invention may also comprise aluminium hydroxide with or without Toll-like receptor agonists as adjuvant.

BRIEF DESCRIPTION OF THE DRAWINGS

The invention is further illustrated by the following examples and the figures, yet without being limited thereto.

FIG. 6: Bivalent vaccines. A-D: Potential epitopes with SYFPEITHI-cores>0 within peptides p9269 (p19$_{136-154}$) (A), p8322 (P19$_{136-151}$) (B), p8461 ($_p$19$_{136-145}$) (C) and p8400 (p19$_{144-154}$) (D). Numerals on the abscissae represent the SYFPEITHI-score of a given peptide, those on the ordinates the number of peptides. Column size represents the number of peptides with the respective SYFPEITHI-Score. E, F: Bivalent vaccinations with peptides from different regions of the same subunit (E) or different subunits (F). 30 µg of each single peptide were injected individually (white columns). When peptides were concomitantly injected (grey column), 15 µg of each peptide was used. Data are given as relative STAT3-phosphorylation as compared to STAT3-phosphorylation of T cells stimulated in the presence of irrelevant serum (anti p4994-serum, black column). Data represent mean of two independent experiments±S.E.M. Sera are pools of five animals each. Both peptides were coupled to KLH.

FIG. 7: Comparison of the immunologic response against IL-23 elicited by p6063 or peptides containing the minimal epitopes—p8400 and p8461—(grey columns) to the responses elicited by peptides derived from sequences mentioned in other patents (open columns) (A). Data are given as relative IL-17 expression as compared to IL-17 expression by splenocytes stimulated in the presence of p6063-serum. Irrelevant serum (anti p4994-serum, black column) was included for control purposes. Data represent mean of two independent experiments±S.E.M. Sera are pools of five animals each. B depicts the position of the peptides relative to the sequence of IL-23p19. The sequence covered by p6063 is shown in bold letters. Grey bars: p6063 and peptides covering minimal epitopes, white bars: peptides from sequences described in foreign patents.

EXAMPLES

Materials and Methods

Mice

Figure 1D:
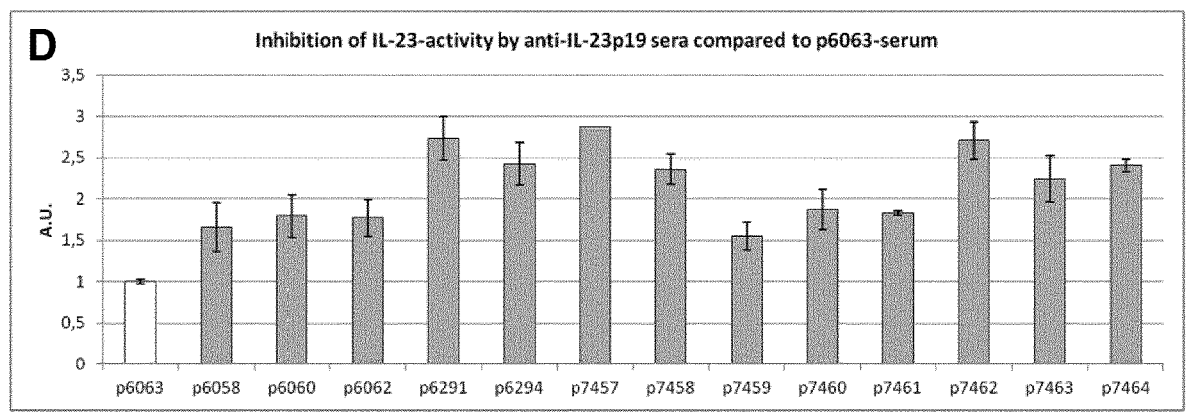
FIG. 1: Inhibition of IL-23 function by sera induced with peptides from p19 as measured with STAT3-assay (A) and splenocyte assay (B) and p40, as measured with STAT3-assay (C): Peptides from p19 and p40 (grey columns) elicit murine sera that inhibit IL-23 function. Serum induced with irrelevant peptide (p4994, black column) was used as negative control. Peptides used for the elicitation of immune sera are denoted on the abscissa, below are the domains in which the respective peptides are situated. Pooled sera from five animals each have been used. The same sera were used for both assays. (D): Lack of inhibition of IL-23 function by sera induced by other p19-derived peptides as measured in the STAT3-assay. Ineffective p19-peptide-induced sera (grey columns) are compared with p6063 serum (white column). Pooled sera from five animals each have been used.
Figure 2A:
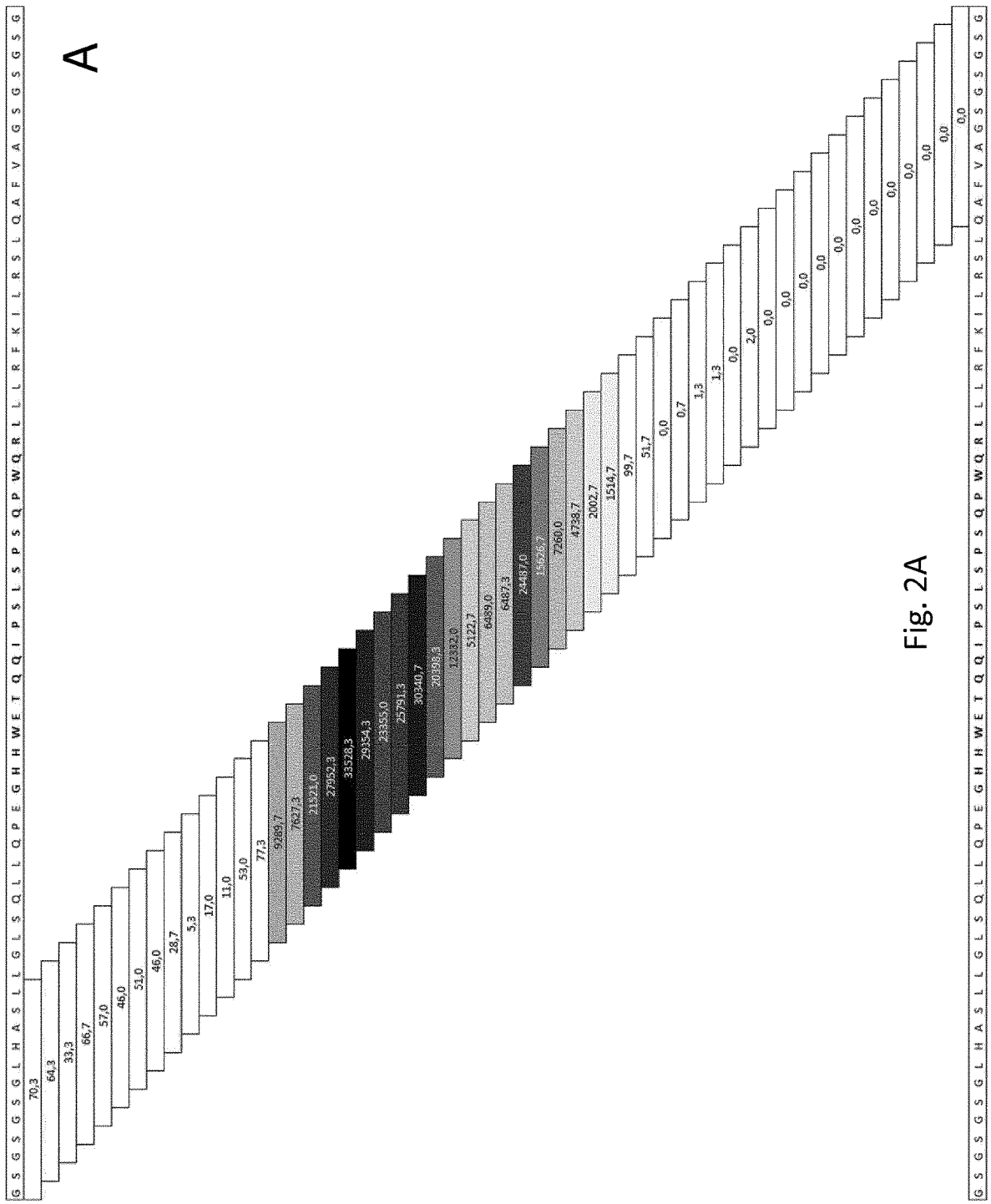
FIG. 2: The p6063-region contains two discrete epitopes. Binding of p6063-specific serum antibodies to a series of overlapping, glass-attached 12-mer peptides on a microarray, sliding by one amino acid, was measured after detection with fluorescence-labelled secondary antibody in a fluorescence-reader. A: Position of the peptides relative to the p19-sequence (upper and lower margin, the sequence of p6063 is printed in bold letters). Data are oD680 and correspond to the amount of antibody bound by a given peptide, darker shades indicate higher values. B: Each of the serial peptides overlaps at least partly with p6063 and is represented by a column. Data are expressed as percentage relative to the strongest binder. The affiliation of a peptide to a certain epitope is indicated by the colour of the column, the sequences of the individual peptides detected by the serum are displayed on the abscissa.
Figure 2B:
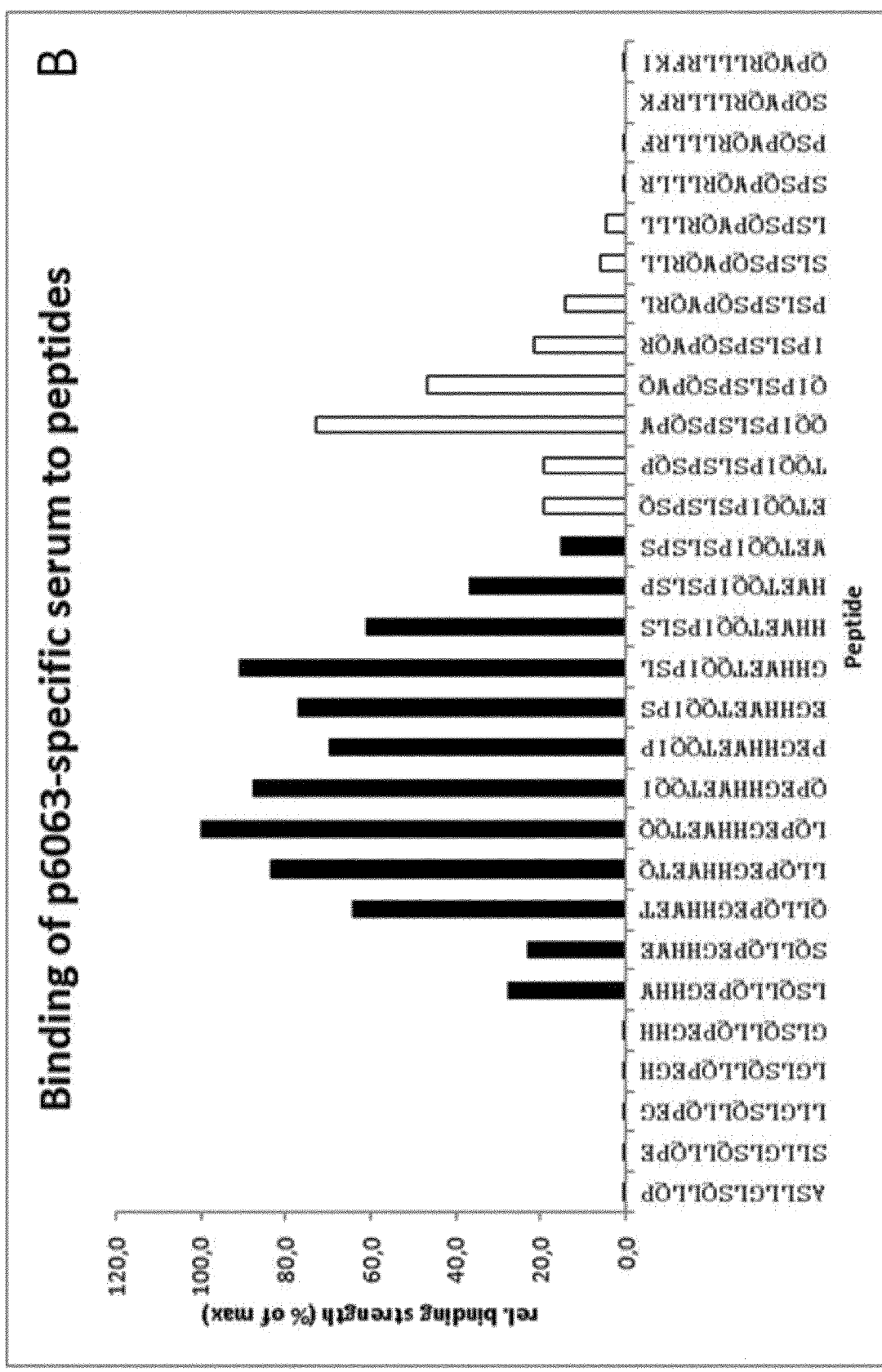
Figure 3:
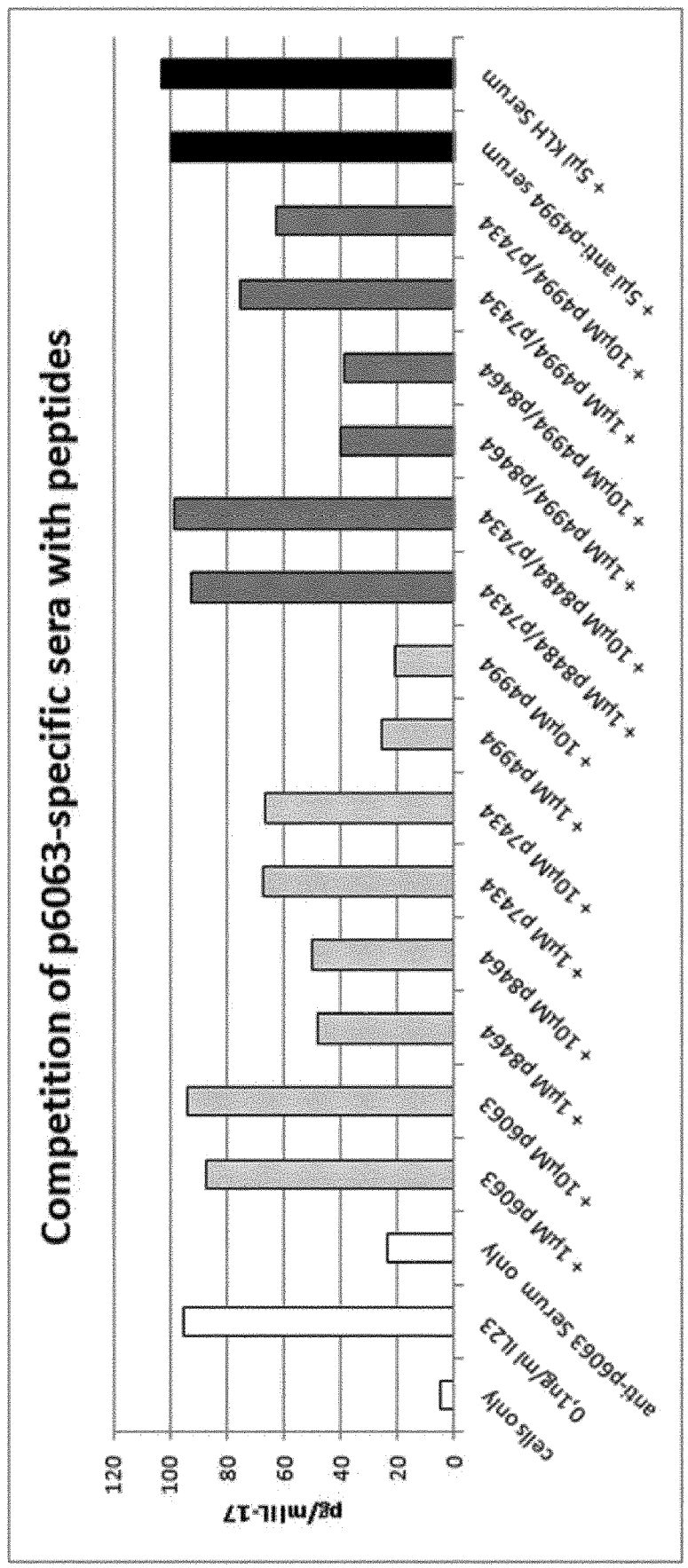
FIG. 3: Competition of the IL-23-inhibitory power of p6063 specific-serum as measured in the splenocyte assay. Peptides were added to the splenocyte assay to compete with IL-23 for binding of serum-antibodies. Open columns: Function controls: stimulation of IL-17-production by IL-23 and anti-p6063-serum-caused inhibition thereof. Black columns: Negative controls with irrelevant sera. Light grey columns: Competition of anti-p6063-serum with single peptides in the indicated concentrations. Dark grey: Competition of anti-p6063serum with combined peptides in the indicated concentrations. The N-terminal competitor was p8464 (p19$_{140-147}$) and the C-terminal p7434 (p19$_{144-158}$). Data are given as percentage of IL-17 expression as compared to splenocytes stimulated in the presence of irrelevant serum (p4994, derived from human C5a). The irrelevant serum was generated with this same peptide. p6063 serum was taken from one single animal with a strong immune response. Control sera are pools from five animals. Serum concentration was 2.5%.
Figure 4:
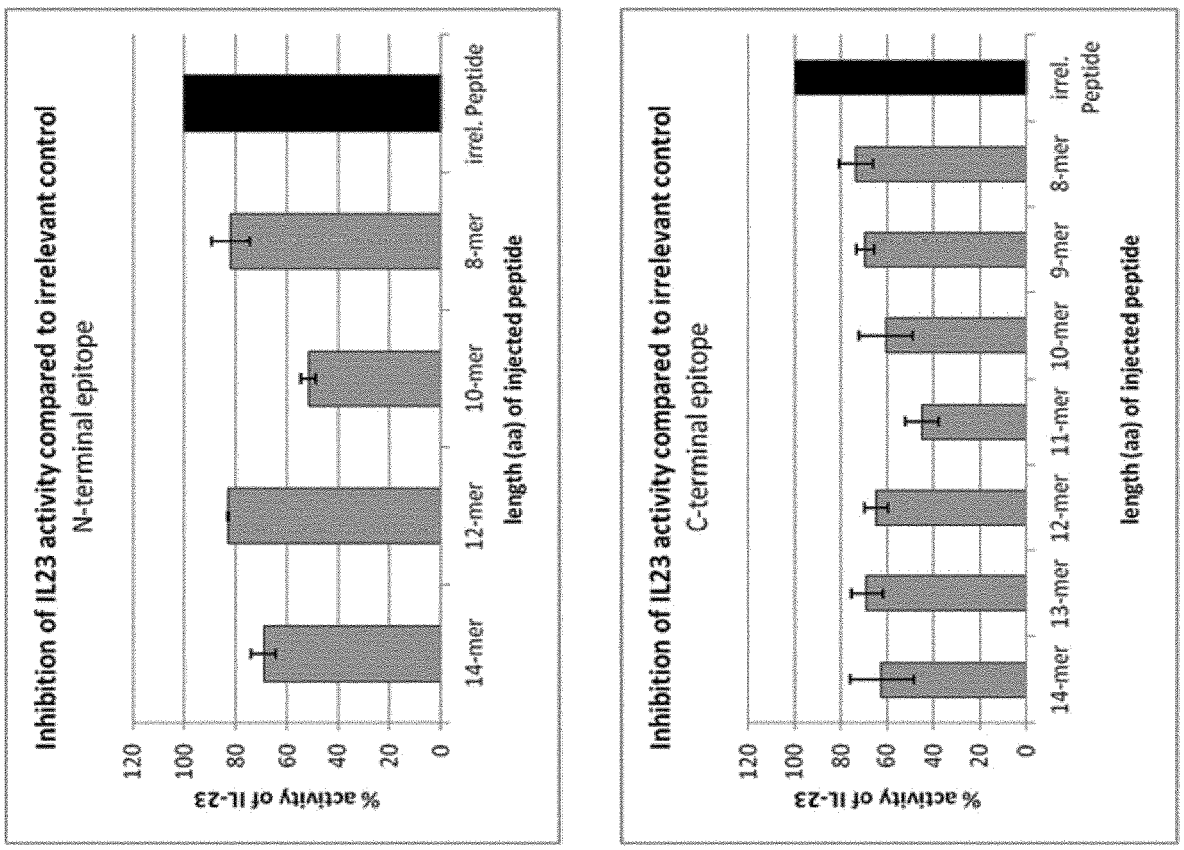
FIG. 4: Search for the minimal immunologically relevant sequences. Truncations were performed in the N-terminal (A) and the C-terminal epitope (B) of domain 3. The panels on the left illustrate the position of the peptides in relation to the sequence of domain 3 (bold letters: p6063); the panels on the right illustrate functional inhibition of IL-17 expression by the respective sera. IL-17A expression as measured by splenocyte assay: cells stimulated with 1 ng/ml IL-23 in the presence of sera raised against the denoted peptides. Data are given as percentage of IL-17 expression as compared to splenocytes stimulated in the presence of irrelevant serum (p4994, black columns). Serum pools from 5 animals are used.

BALB/cj and C57BL/6j mice were purchased from Charles River (Sulzfeld, Germany) or Janvier (St. Berthevin, France)

All animal testing was performed in accordance with actual Austrian national law (Tierversuchsgesetz 2012-TVG 2012) and with consent of the relevant authorities.

Peptides

Peptides were purchased from EMC Microcollections GmbH (Tübingen, Germany). All peptides are derived from IL-23 sequences, with the exception of the irrelevant peptide p4994 which is derived from human C5a and bears no relevant similarity to either subunit of IL-23.

Sequences

GenBank sequences AAH66268.1 (for p19) and AAD56386.1 (for p40) were chosen as templates for the sequences and numeration of the vaccination peptides. They represent the complete sequences of the cytokine subunits including the putative leader sequences. These sequences are representative, since they have 100% sequence homology to the vast majority of the sequences of the complete IL-23 subunit proteins retrievable by GeneBank and SwissProt. Peptide sequences were tested with blastp for IL-23 specificity.

Coupling of Peptides

KLH (SIGMA-ALDRICH, St. Louis, Mo. or biosyn Arzneimittel GmbH, Fellbach, Germany) is activated by incubation with N-gamma-maleimidobutyryl-oxysuccinimide ester (GMBS; AppliChem, Darmstadt, Germany) for 30 min at RT at a weight ratio of 1:2 and then dialyzed against Na-phosphate buffer (pH 6.7). 1 mg/ml peptide with a N- or C-terminally added Cysteine in 10% DMSO/20 mM Na-phosphate buffer (pH 6.8) is added to an equal volume of activated KLH and incubated for two hours at RT. Coupling efficiency is tested in an Ellmann assay or HPLC.

CRM197 (Pfenex Inc., San Diego, Calif.) is activated by incubation with N-gamma-maleimidobutyryl-oxysuccinimide ester (GMBS; AppliChem, Darmstadt, Germany) for 30 min at RT and then dialyzed against Na-phosphate buffer (pH 6.7). 1 mg/ml peptide with a N- or C-terminally added Cysteine in 10% DMSO/10 mM Na-phosphate buffer (pH 6.8) is added to an equal volume of activated CRM and incubated for two hours at RT. Coupling efficiency is tested by HPLC.

Preparation of the Vaccines

Carrier-coupled peptide is diluted in 1×PBS and water to a final net peptide-concentration of 150 µg/ml and sterile-filtered through a 0.22 µm-mesh. Then ¹⁄₁₀ Vol 10 mg/ml Alum (Brenntag Biosector A/S, Frederiksund, DK) is added. The vaccine is aliquoted, incubated for 1h at RT and stored at 4° C. until use.

Immunization of Mice

Vaccines are vortexed and applied subcutaneously in the flank of mice (30 µg net AFFITOPE© in 200 µl) with an insulin syringe with a G30-gauge (Omnican©50, B.Braun Melsungen AG, Melsungen, Germany). Vaccination is repeated four times, on days 0, 14, 28 and 42. Mice are monitored one hour after injection for symptoms of distress. Typically, one peptide is tested in a group of five mice. When binary vaccines were tested, 15 µg of each AFFITOPE© were successively applied in separate injections in both flanks of the same animal.

Collection of Sera

Pre-plasma as well as the control plasma after the second and third vaccinations are taken by tail-clipping. 20 µl of blood are taken from the tail vein with an EDTA-coated capillary (Hirschmann Laborgeräte, Eberstadt, Germany) and blown out of the capillary into an Eppendorf-tube, containing 180 µl PBS. The tube is centrifuged at 13000×g for 10 min. at 4° C., then the supernatant is transferred to a new tube and frozen at −80° C. until further analysis.

For the collection of the final serum, mice are deeply anaesthesized. Blood is quantitatively—typically 600 µl—collected from the animals in a serum tube (BD Microtainer, Becton Dickinson, Heidelberg, Germany). The tubes are left for 30 min. at RT, then centrifuged at RT for 3 min at 2000×g. The supernatant is collected and transferred to an Eppendorf-tube and frozen at −80° C. until further analysis.

After blood collection, mice are sacrificed by cervical dislocation.

Testing of Sera

Response to Injected Peptide

BSA-coupled peptide (1 µM, 50 µl) is bound to 96-well plates. Plates are incubated o/n at 4° C., then blocked after removal of unbound peptide for one hour at 37° C. with blocking buffer (PBS/1% BSA). After removal of blocking buffer, 50 µl of serum is added to each well in serial 1:2 dilution steps with dilution buffer (PBS/0.1% BSA, 0.1% Tween20) starting with a dilution of 1:100. After one hour at 37° C., the supernatant is removed and the plates are washed three times (PBS, 0.1% Tween20). 50 µl of biotinylated anti-mouse IgG (Southern Biotech, Birmingham, Ala., USA) at a concentration of 0.25 µg/ml are added and incubated for one hour at 37° C. Unbound antibody is removed by three subsequent washing steps. 50 µl/well (0.25 U/ml) of Streptavidin-horseradish peroxidase (Roche, Mannheim, Germany) are added and plates are incubated for 30 minutes at 37° C. After three washes, 50 µl of ABTS substrate solution (0.068 µM ABTS (AppliChem) in 0.1M Citric acid, pH 4.3) with $H_2O_2$ (1:1000) are added to each well and incubated at RT for 40 minutes. The reaction is stopped by addition of 50 µl stop solution (1% SDS in water). Serum antibody concentrations are then measured on a Microwell reader (BioTek Power Wave 340 (BioTek, Winooski, Vt., USA) or Tecan Sunrise (Tecan Group Ltd., Männedorf, Switzerland)) at 405 nm.

Crossreactivity to IL-23 rhu IL-23 (HumanZyme, Chicago, Ill., USA) at a concentration of 0.5 µg/ml is deployed in 50 µl aliquots in the wells of a 96-well plate. Plates are incubated o/n at 4° C. After removal of unbound coating agent, prediluted serum is added to each well at ascending dilution rates. After one hour at 37° C., the supernatant is removed and the plates are washed three times (PBS, 0.1% Tween20). 50 µl of biotinylated anti-mouse IgG at a concentration of 0.25 µg/ml are added and incubated for one hour at 37° C. Unbound antibody is removed by three subsequent washing steps. 50 µl/well of streptavidin-horseradish peroxidase (0.25 U/ml) are added and plates are incubated for 30 minutes at 37° C. After three washes, 50 µl of ABTS substrate solution (0.068 µM ABTS in 0.1M Citric acid, pH 4.3) with $H_2O_2$ (1:1000) are added to each well and incubated at RT for 40 minutes. The reaction is stopped by addition of 50 µl stop solution (1% SDS in water). Serum antibody concentrations are then measured on a Microwell reader at 405 nm.

Splenocyte Assay

IL-23-induced production of IL-17A by splenocytes and its suppression by serum antibodies is measured as published (Aggarwal et al., 2003). Briefly, spleens are excised from sacrificed C57BL/6j mice and splenocytes are singularized by mechanical disruption accompanied by DNAse I (20 µg/m1)- and Collagenase D (100 Mandl Units/m1)-digest (both supplied by Roche). After removal of erythrocytes, cells are resuspended in RPMI supplemented with 10% FCS and 4 ng/ml rmuIL-2 (e-Bioscience, San Diego Calif., USA) at a concentration of $2.5 \times 10^6$ cells/ml. Cells are stimulated with 0.1 ng/ml rhuIL-23 (R&D systems, Minneapolis, Minn., USA) and deployed in 200 µl aliquots on the plates. 5 µl of the sera to be tested are added to each well. The plates are incubated for three days at 37° C./5% $CO_2$, after which the supernatants are collected and frozen at −80° C. until further analysis.

The analysis for IL-17A is performed with the IL-17A (homodimer) ELISA Ready-SET-Go!© Kit (eBioscience) strictly following the instructions of the manufacturer.

Results for serum-inhibited IL-17A-expression are calculated as:

$$\% \text{ Expression} = 100 \times \frac{\text{Expression}(IL-23 + \text{probe}) - \text{Expression}(\text{background})}{\text{Expression}(IL-23 + \text{irrelevant probe}) - \text{Expression}(\text{background})}$$

STAT3 Assay

Phosphorylation of STAT3 of primary human lymphocytes is measured by flow Cytometry ((Krutzik and Nolan, 2003), modified)). Briefly, PBMC (isolated either from freshly collected blood or from Buffy coats from the Austrian Red Cross are resuspended in RPMI1640 and stimulated for three days with anti-CD3, anti-CD28 mAbs (both from Miltenyi Biotech GmbH, Bergisch Gladbach,Germany) and rhuIL-2 (eBioscience or R&D systems). After three washes in ice-cold PBS, the T cell blasts are resuspended in PBS, aliquoted to $2 \times 10^5$ cells/200µl and stimulated with 5 ng/ml rhu IL-23 (eBioscience) with or without IL-23-inhibiting agents. After incubation for 20 minutes at 4° C., cells are fixed and permeabilized using the BD Phosflow™ Kit (Becton Dickinson) following the instructions of the manufacturer. The antibody used for intracellular staining of phosphorylated STAT3 is mouse Anti-human STAT3 (pY705)-Alexa Fluor® 488. Mouse anti-human CD4-APC is used for counterstaining (both antibodies supplied by Becton Dickinson). Alexa Fluor® 488-fluorescence of the CD4$^+$ T cell blasts is measured on a FACSCanto II Flow Cytometer (Becton Dickinson).

Serum-caused reduction of STAT3-phosphorylation is calculated as:

$$\% \text{ Expression} = 100 \times \frac{\text{Expression}(IL-23+\text{probe}) - \text{Expression}(\text{unstimulated})}{\text{Expression}(IL-23+\text{irrelevant probe}) - \text{Expression}(\text{unstimulated})}$$

Fine Epitope Mapping

Microarray-based fine epitope mapping was performed by PEPperPRINT GmbH (Heidelberg, GE) using the PEPperMAP© technology. Briefly, the sequence of the domain 3 and its immediate surroundings was split into overlapping 12 mer peptides, sliding by one amino acid. The resulting peptides were spotted in triplicate on a glass slide. These treated slides were incubated with diluted murine anti-p6063-serum. Secondary goat anti-mouse IgG (H+L) DyLight680 antibody was used to detect serum antibodies. Fluorescence intensity was measured with a LI-COR Odyssey Imaging System (LI-COR Biosciences, Nebr., US) and quantified.

In Silico Analyses

SYFPEITHI was used to predict MHC class I and II affinities of fragments contained in vaccination peptides of different length. PAProC was used to predict proteasomal cleavage sites.

| Sequences | | | |
|---|---|---|---|
| Name | SeqID | Position | Sequence |
| IL-23p19 | 1 | $p19_{1-189}$ | GenBank AAH66268.1 |
| IL-23p40 | 2 | $p40_{1-328}$ | GenBank AAD56386.1 |
| p6058 | 3 | $p19_{20-33}$ | RAVPGGSSPAWTQC |
| p6059 | 4 | $p19_{42-59}$ | C-TLAWSAHPLVGHMDLREE |
| p6294 | 5 | $p19_{46-59}$ | C-SAHPLVGHMDLREE |
| p7457 | 6 | $p19_{51-72}$ | C-VGHMDLREEGDEETTNDVPHIQ |
| p7458 | 7 | $p19_{51-72}$ | VGHMDLREEGDEETTNDVPHIQ-C |
| p7459 | 8 | $p19_{90-110}$ | C-LQRIHQGLIFYEKLLGSDIFT |
| p7460 | 9 | $p19_{90-110}$ | LQRIHQGLIFYEKLLGSDIFT-C |
| p6061 | 10 | $p19_{100-119}$ | C-YEKLLGSDIFTGEPSLLPDS |
| p6060 | 11 | $p19_{100-129}$ | C-YEKLLGSDIFTGEPSLLPDSPVGQLHASLL |
| p6291 | 12 | $p19_{105-121}$ | C-GSDIFTGEPSLLPDSPV |
| p6062 | 13 | $p19_{121-135}$ | C-VGQLHASLLGLSQLL |
| p7461 | 14 | $p19_{130-149}$ | C-GLSQLLQPEGHHWETQQIPS |
| p7462 | 15 | $p19_{130-149}$ | GLSQLLQPEGHHWETQQIPS-C |
| p6063 | 16 | $p19_{139-159}$ | C-GHHWETQQIPSLSPSQPWQRL |
| p7463 | 17 | $p19_{167-188}$ | C-RSLQAFVAVAARVFAHGAATLS |
| p7464 | 18 | $p19_{167-188}$ | RSLQAFVAVAARVFAHGAATLS-C |
| p7434 | 19 | $p19_{144-158}$ | C-TQQIPSLSPSQPWQR |
| p8464 | 20 | $p19_{140-147}$ | C-HHWETQQI |
| p7432 | 21 | $p19_{138-158}$ | C-EGHHWETQQIPSLSPSQPWQR |
| p8320 | 22 | $p19_{132-151}$ | C-SQLLQPEGHHWETQQIPSLS |
| p8321 | 23 | $p19_{134-151}$ | C-LLQPEGHHWETQQIPSLS |
| p8322 | 24 | $p19_{136-151}$ | C-QPEGHHWETQQIPSLS |
| p8323 | 25 | $p19_{138-151}$ | C-EGHHWETQQIPSLS |
| p8459 | 26 | $p19_{136-149}$ | C-QPEGHHWETQQIPS |
| p8460 | 27 | $p19_{136-147}$ | C-QPEGHHWETQQI |
| p8461 | 28 | $p19_{136-145}$ | C-QPEGHHWETQ |
| p8462 | 29 | $p19_{136-143}$ | C-QPEGHHWE |
| p8397 | 30 | $p19_{144-157}$ | C-TQQIPSLSPSQPWQ |
| p8398 | 31 | $p19_{144-156}$ | C-TQQIPSLSPSQPW |
| p8399 | 32 | $p19_{144-155}$ | C-TQQIPSLSPSQP |
| p8400 | 33 | $p19_{144-154}$ | C-TQQIPSLSPSQ |
| p8761 | 34 | $p19_{144-153}$ | C-TQQIPSLSPS |
| p8762 | 35 | $p19_{144-152}$ | C-TQQIPSLSP |
| p8763 | 36 | $p19_{144-151}$ | C-TQQIPSLS |
| p8332 | 37 | $p19_{137-146}$ | C-PEGHHWETQQ |
| p8333 | 38 | $p19_{155-164}$ | C-PWQRLLLRFK |
| p8337 | 39 | $p19_{127-137}$ | C-SLLGLSQLLQP |
| p8759 | 40 | $p19_{137-155}$ | C-PEGHHWETQQIPSLSPSQP |
| p7977 | 41 | $p19_{160-179}$ | C-LLRFKILRSLQAFVAVAARV |
| p9165 | 42 | $p19_{52-59}$ | C-PSQPWQRL |
| p9269 | 43 | $p19_{36-54}$ | C-QPEGHHWETQQIPSLSPSQ |
| p6449 | 44 | $p40_{35-49}$ | C-LDWYPDAPGEMVVLT |
| p4994 | 45 | $C5a_{55-74}$ | CVVASQLRANISHKDMQLGR |

List of sequences used in this study. "C-" followed or "-C" preceded by the sequence indicates that the cysteine needed to attach the peptide to the carrier is not part of the original protein-sequence, while "C" followed preceded by the sequence indicates a naturally occurring Cysteine; peptide names ("pXXXX") for the C-coupled peptide and the peptide without added C are the same due to the identical core sequence.

| Name | SeqID | Position | Sequence |
|---|---|---|---|
| p6063 | 16 | $p19_{139-159}$ | C-GHHWETQQIPSLSPSQPWQRL |
| p8322 | 24 | $p19_{136-151}$ | C-QPEGHHWETQQIPSLS |
| p8461 | 28 | $p19_{136-154}$ | C-QPEGHHWETQ |
| p8400 | 33 | $p19_{144-154}$ | C-TQQIPSLSPSQ |
| p9269 | 43 | $p19_{136-154}$ | C-QPEGHHWETQQIPSLSPSQ |
| p9440 | 46 | $p19_{136-153}$ | C-QPEGHHWETQQIPSLSPS |
| p9441 | 47 | $p19_{136-152}$ | C-QPEGHHWETQQIPSLSP |

List of claimed sequences. "C-" followed or "-C" preceded by the sequence indicates that the cysteine needed to attach the peptide to the carrier is not part of the original protein-sequence, while "C" followed preceded by the sequence indicates a naturally occurring Cysteine Results Definition of Region of Interest (Domain 3/p6063)

To be qualified as a potential vaccine, a peptide is required to elicit sera which fulfil three conditions: The serum must a) react with the immunizing peptide, b) crossreact with the original target, i.e.: IL-23 and c) interfere with IL-23 function. Every peptide used for immunization in this study was assayed for these conditions.

Screening for Epitopes that Induce IL-23 Binding Sera

We used 16 overlapping peptides to screen the p19 subunit for immunogenic regions. The peptides were N- or C-terminally linked to the carrier and cover approximately 90% of the sequence. While all elicited sera were able to bind the immunizing peptides (data not shown), we found that 14/16 sera contained antibodies that crossreacted with rhuIL-23 (Tab. 1). Likewise, the target region of Ustekinumab was demonstrated to contain immunogenic regions to obtain data which would allow us comparison with peptides from a known immunogenic region (Tab. 1).

Screening for Functionally Relevant Epitopes

To determine whether the peptide-specific sera were able to interfere with IL-23 function, we employed two assays: Firstly the splenocyte assay, where we used rhu-IL-23 to stimulate IL-17A production in murine cells, and secondly the STAT3-assay that uses primary human cells as a read-out for rhuIL-23 function via STAT3-phosphorylation upon binding of the human IL-23 receptor.

Figure 5:
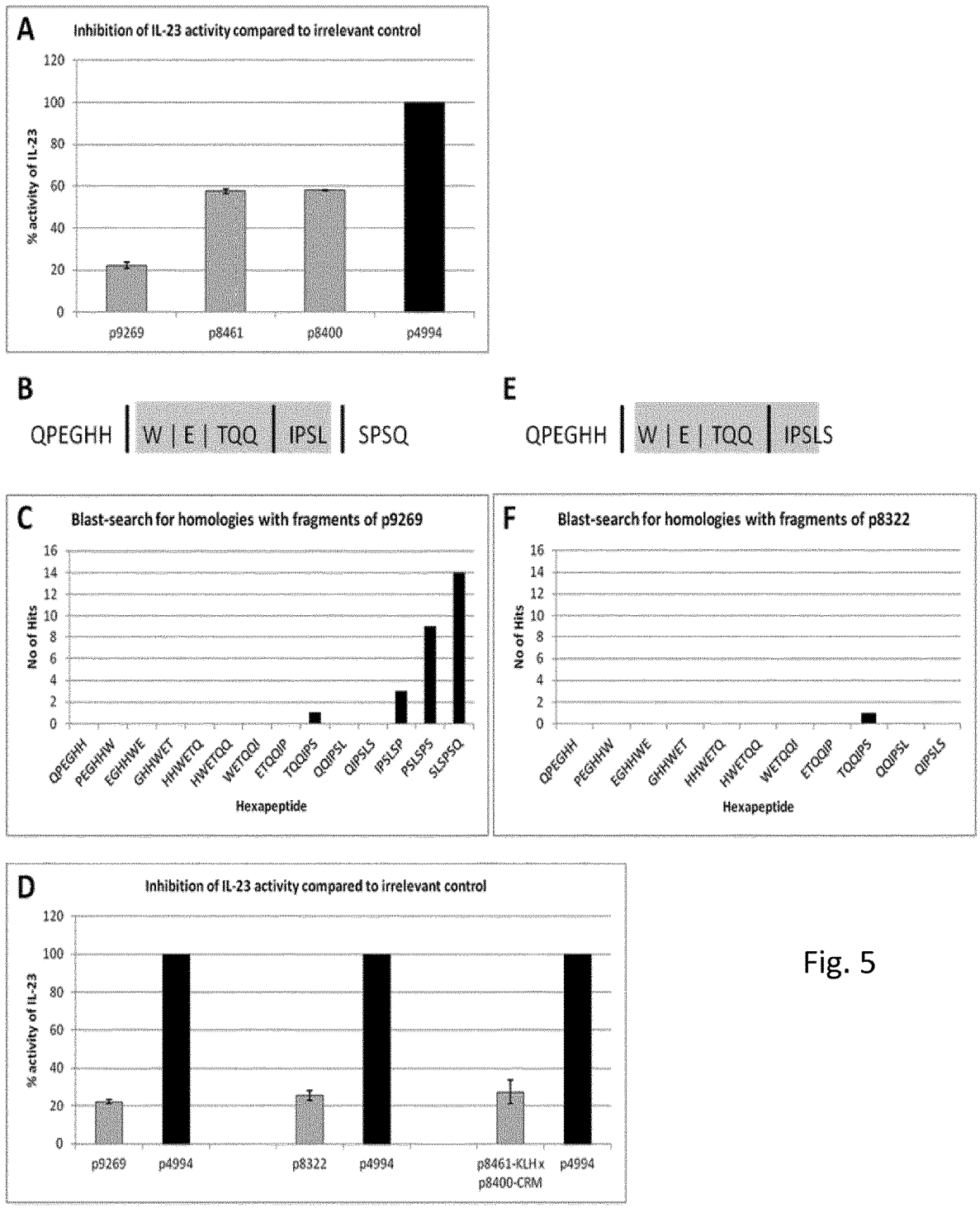
FIG. 5: Biepitopic and bivalent vaccines. A: Comparison of serum elicited against the biepitopic peptide p9269 with sera against the monoepitopic peptides p8461 and p8400. IL-17A expression as measured by splenocyte assay: cells stimulated with 1 ng/ml IL-23 in the presence of sera raised against the denoted peptides. Data are given as percentage of IL-17 expression as compared to splenocytes stimulated in the presence of irrelevant serum (p4994, black columns) B: Potential proteasomal cleavage sites in p9269. The size of the black bars between letters indicates the probability of cleavage. The area shaded in gray highlights a sequence predicted to be a strong MHC I-binder (See Tab 2). C: Homologies of p9269-derived hexapeptides with unrelated proteins. The size of the bars correlates to the number as indicated on the y-axis of proteins with homology to a given hexamer, indicated on the x-axis. D: Comparison of IL-23 inhibitory capacity of p9269 (left pair of columns), p8322 (middle pair of columns) and p8461 concomitantly injected with p8400 (right pair of columns)—triggered sera. Results are compiled from multiple independent experiments and shown as mean values±S.E.M. Details as in (A). E: Potential proteasomal cleavage sites in p8322. Details as in (B). F: Homologies of p8322-derived hexapeptides with unrelated proteins. Details as in (C).

We found three regions in IL-23p19 containing immunogenic epitopes that repeatedly induced functionally relevant antibodies (FIGS. 1A and B). These regions were dubbed domain 1, 2 and 3 respectively. p6059 ($p19_{42-57}$) is situated in domain 1. In crystal structure models of the cytokine, this domain was found to be situated on the interface between the two subunits. p6061 ($p19_{100-119}$) and p6063 ($p19_{139-159}$) are situated in domains 2 and 3, respectively. These domains are situated facing outward of the complex according to the models and thus are likely to be accessible for antibodies. They therefore represent promising targets for immunologic intervention against IL-23. The peptide from the Ustekinumab target region, p6449 ($p40_{35-49}$) also inhibits IL-23 function (FIG. 1C). It is situated on a loop on the far end of the large subunit facing outward.

Data from p-19-peptide-induced sera not inhibiting IL-23 function are depicted in FIG. 1D.

Of the tested peptides, p6063 ($p19_{139-159}$) repeatedly elicited the most potent IL-23-inhibiting sera. Thus, we chose to focus on domain 3 for the development of an anti-IL-23 vaccinating agent. The location of domain 3 suggests that functional inhibition of IL-23 by domain-specific sera occurs via an inhibition of IL-23/IL-23R interaction.

Fine Epitope Analysis of Domain 3

Exact epitope mapping surprisingly revealed the presence of two close yet discrete epitopes in the p6063 region. Intriguingly, antibodies from anti-p6063 serum recognize two different regions, as demonstrated by microarray-based binding studies (FIG. 2). FIG. 2 includes SEQ ID No. 140, and 29 12-mer peptide fragments of SEQ ID No. 140.

In order to confirm the epitope-specificity of the functionally relevant antibodies contained within p6063 serum, we added p6063 peptide to the splenocyte assay to provide a specific competitor to IL-23 for the serum antibodies. Indeed, addition of this peptide abolished IL-23 inhibition completely, whereas addition of irrelevant peptide (p4994) did not interfere with inhibition, corroborating that it is an effect caused by specific antibodies and not by unspecific interference. (FIG. 3).

To confirm these findings and to generate supplementary information about the exact location of the two discrete epitopes, we used truncated forms of the p6063 peptide, namely p8464 ($p19_{140-147}$) from the N-terminus and p7434 $p19_{144-158}$) from the C-terminus as competitors. Both peptides were able to abolish IL-23-inhibition only partly, corroborating that a) the p6063 region contains more than one relevant epitope and b) these peptides indeed competed with different epitopes for the serum antibodies (FIG. 3). Consequently, combined addition of p8464 and p7434 to the assay leads to blocking of inhibition equal to the one obtained with p6063. Combining either truncated peptide with the irrelevant peptide did not result in synergistic effects (FIG. 3).

Definition of Minimal Epitopes

Aiming at the definition of the minimal core sequences, we vaccinated mice with successively truncated forms of peptides contained within domain 3.

To define the N-terminal epitope we started with the 14-mer p8459 ($p19_{136-149}$) which contains the p8464 peptide as core with extensions both N- and C-terminally. C-terminal truncations were performed in steps of two amino acids to define the demarcation against the C-terminal epitope. The best results were obtained with the p8461 ($p19_{136-145}$) 10-mer QPEGHHWETQ (SEQ ID No. 98) (FIG. 4A). FIG. 4A also shows residues 12-45 of SEQ ID No. 140.

To define the minimal sequence of the C-terminal epitope, we started with the 14-mer p8397 ($p19_{144-157}$). This peptide is a truncated version of p7434 and as such mimics the second epitope in domain 3. It was subsequently cropped C-terminally in steps of one amino acid. While all truncated peptides yielded functionally active sera, the best results were obtained with the 11-mer p8400 ($p19_{144-154}$) TQQIPSLSPSQ (SEQ ID No. 99) (FIG. 4B). FIG. 4B also shows residues 12-45 of SEQ ID No. 140.

Combination Strategies: Biepitopic Peptides and Binary Vaccines

In an attempt to further increase functional inhibition of IL-23, we injected mice with vaccines containing two immunogenic epitopes at once. The idea behind this is that immunologic attack of different sites of the same molecule/complex might not only interfere more effectively with receptor binding but is also expected to increase clearance of the organism by more polyclonal opsonisation of the target and subsequent crossactivation of phagocytic cells.

We employed two different strategies towards that aim: On one hand, we used biepitopic vaccines, on the other hand binary vaccines.

Biepitopic Vaccines

Biepitopic vaccines contain longer peptides combining two epitopes. Possible scenarios include naturally occurring stretches of epitopes in either their original or altered sequence, or the combination of epitopes from distant locations on the same or even different subunits of the complex, joined in one peptide, possibly separated by a spacer. To confirm our concept we used the peptide p9269 ($p19_{136-154}$), which corresponds to the original IL-23p19-sequence spanning p8461 and p8400. Indeed, the serum elicited by p9269 inhibited IL-23-function more effectively than each of the sera against p8461 and p8400 alone (FIG. 5A).

The use of peptides as immunogens harbours two potential safety hazards: First the presence of MHC class I epitopes in the sequence of the peptide and secondly cross-reactivity of the sera with other, unrelated proteins. In the first case, scenarios are conceivable, where vaccination peptides enter the MHC class I pathway, which could lead to the generation of a peptide-fragment-specific cytotoxic T cell response that might in turn be aimed against IL-23 producing cells and thus cause severe cell/tissue damage. This scenario is clearly undesirable. To address this question, we subjected p9269 to SYFPEITHI, an algorithm designed to calculate MHC class I binding peptides in a given sequence. The algorithm predicted seven potential strong MHC class I binders, consisting of four different sequences with a predilection for five different MHCI-alleles (Tab. 2). A second algorithm, PAProC, revealed that one of these sequences could be generated by proteasomal degradation (FIG. 5B).

We addressed the second question by fragmenting the sequence of p9269 into overlapping hexapeptides and performing BLAST-searches against the SWISS-Prot database.

27 homologies with unrelated proteins were found (FIG. 5C). Interestingly, the vast majority of the homologies are linked to the three C-terminal amino acids of p9269. If the BLAST-search for linear homologies is extended to a sequence elongated by one C-terminal amino acid—as would be p8759—one protein with a heptapeptide homology and five more proteins with hexapeptide-homologies can be found, not counting their various splice-variants.

It is conceivable that a truncation of p9269 by one, preferably two or even three C terminal amino acids should remedy both potential safety shortcomings, while still addressing both epitopes of domain 3. Omitting the three C-terminal amino acids of p9269 results in the 16-mer p8322 ($p19_{136-151}$). This peptide indeed elicits sera with IL-23-inhibiting capacity similar to p9269 (FIG. 5D). While SYFPEITHI predicts six of the seven strong MHC class I binders as in the longer peptide, these fragments cannot be generated by proteasomal degradation according to PAProC (FIG. 5E). On the other hand, only one of the 27 hexapeptide homologies to unrelated proteins identified in p9269 remains in p8322 (FIG. 5F). FIGS. 5B, 5C, 5E and 5F include SEQ ID No. 100, and fragments of SEQ ID No. 100.

Taken together, these results indicate that biepitopic peptides can be more powerful in eliciting anti-IL-23 immunity than single monoepitopic peptides and can be designed to be satisfactorily safe.

Binary Vaccines

In binary vaccines, two monoepitopic peptides are concomitantly applied to the subject. Possible scenarios involve peptides from the same domain, from spacially distinct domains of from different subunits of a molecule/complex or even different targets. Peptides can be coupled to the same or to different carriers, the latter to avoid carrier-dependent epitope inhibition.

To confirm this concept, we injected mice with separate vaccines containing p8461 coupled to KLH and p8400 coupled to CRM197 applied in separate locations (i.e.: in opposing flanks). Bivalent vaccines indeed repeatedly effectuated powerful anti-IL-23 responses similar to the biepitopic peptides described above (FIG. 5D).

To address safety issues, we used the SYPPEITHI-algorithm to search for possible MHC Class I and MHC Class II binding peptides contained in the p9269 ($p19_{136-154}$) 19-mer (FIG. 6A), in the p8322 ($p19_{136-151}$) 16-mer (FIG. 6B) and in the peptides containing the minimal epitopes, the N-terminal p8461 ($p19_{136-145}$) 10-mer (FIG. 6C) and the C-terminal p8400 ($p19_{144-154}$) 11-mer (FIG. 6D). All three peptides were subjected to epitope-search for 8- to 15-mers in a totality of the 124 n-mer/MHC I/II-combinations available in SYFPEITHI. Indeed, a clear correlation between the length of the analyzed peptide and the amount of potential epitopes is apparent: p9269 contains 603 possible peptides with a SYFPEITHI-score>0, of which seven MHC class I binders display a score≥20 (See Tab 2), making them potential strong MHC binders. p8322 contains 368 possible peptides with a SYFPEITHI-score>0, among them six putative strong binders as in p9269, as mentioned above. p8400 contains 142 and p8461 only 75 possible peptides with a SYFPEITHI-score>0. Neither short peptide contains potential high-binders. According to PAProC, no fragments long enough for MHC I-binding can be generated by proteasomal cleavage from p8461 or p8400 (not shown).

Further experiments demonstrate that the concept of bivalent vaccines yields also beneficial results, when the monovalent vaccines are coming from different domains of the same subunit (i.e.: p6061 ($p19_{100-119}$) from domain 2 and p6063 ($p19_{139-159}$) from domain 3 of the p19 subunit (FIG. 6E) or from different subunits (i.e.: p6063 from the small subunit and p6449 ($p40_{35-49}$) from the large subunit) (FIG. 7F). FIG. 7B includes SEQ ID No. 141.

Taken together, these results show powerful anti-IL-23 responses elicited by bivalent vaccines and indicate that the use of shorter peptides precludes safety issues in the context of target-mediated cytotoxic responses.

Delimitation Against Previously Published Peptides

Peptides derived from sequences in or in the immediate vicinity of domain 3 described in other patents have been synthesized with a N-terminal cysteine, coupled to KLH and injected in mice. The resulting sera have been tested for anti-IL-23 activity (FIG. 7).

When tested in two independent experiments, p8461 ($p19_{136-145}$) reduced IL-17 expression by splenocytes to 26.2±4.5% and p8400 ($p19_{144-154}$) to 34.6±3.0%. p6063 ($p19_{139-159}$) reduced IL-17 expression by splenocytes to 23.6±2.5% as compared to an irrelevant serum.

p8332 ($p19_{137-146}$) (i.e.: PEGHHWETQQ (residues 2-11 of SEQ ID No. 107)) and p8333 ($p19_{155-164}$) (i.e,: PWQRLLLRFK (SEQ ID No. 38)) are taken from EP 2 392 597 A2 [Lewis], where they are mentioned as target-sequences for bispecific antibodies against IL-23 and IL-17A. Serum elicited to p8332 inhibits IL-23 function 48% less effectively then serum against p6063, and, importantly, 33% less effectively than serum elicited against the closely overlapping p8461. p8333-serum inhibits IL-23 300% less efficiently than p6063-serum, similar to the irrelevant serum p8337 ($p19_{127-137}$) (i.e.: SLLGLSQLLQP (SEQ ID No. 39)) was described in WO 2007/005955 A2 [Benson], where it represents a target site for engineered anti-IL-23 antibodies. The resulting serum also reduced expression of IL-17A to a degree similar to the irrelevant control serum.

p8759 ($p19_{137-155}$) (i.e.: PEGHHWETQQIPSLSPSQP (SEQ ID No. 120)) was mentioned in WO 2005/108425 A1 [Bachman/Cytos] as possible peptide sequence to be used for anti-IL-23 immunization after coupling to a virus-like particle, although no immunization studies were shown using this or any other IL-23p19-derived peptide. The resulting serum reduced expression of IL-17A 92% less effectively than p6063-derived serum, 31% less effectively than p8400-derived serum and 73% less effectively than p8461-derived serum.

p7977 ($p19_{160-179}$) (i.e.: LLRFKILRSLQAFVAVAARV (SEQ ID No. 132)), described in WO 03/084979 A2 [Zagury] as possible agent for anti-cytokine immunization is situated C-terminally of the p6063-region. Serum elicited with this peptide reduced IL-17A-expression 275% less effectively than p6063-derived serum serum.

p9165 ($p19_{152-159}$) (i.e.: PSQPWQRL (SEQ ID No. 42)) as mentioned WO 2007/027714 A2 [Presta] where it reporesents a target site for engineered anti-IL-23 antibodies, is situated at the C-terminal end of p6063. Serum elicited with this peptide reduced IL-17A-expression also only in the same range as the irrelevant serum.

These data demonstrate that peptides we had defined to contain the minimal epitopes for the N-terminal epitope—i.e.: p8461 ($p19_{136-145}$) and the C-terminal epitope—i.e.: p8400 ($p19_{144-154}$) as well as the longer p6063 elicited sera are superior in suppressing IL-23 activity to overlapping sequences earlier described.

Graphs & Tables

TABLE 1

Peptides used to scan IL-23p19 and the Ustekinumab-region for immunogenic regions. "C-" followed or "-C" preceded by the sequence indicates that the cysteine needed to attach the peptide to the carrier is not part of the original protein-sequence, while "C" preceded by the sequence indicates a naturally occurring cysteine. Sera were deemed binding, when the minimal dilution factor to attain oDmax/2 was at least 1: 100.

| Name | SeqID | Position | Sequence | Titer[1] | Functional relevance[2] |
|---|---|---|---|---|---|
| p6058 | 3 | $p19_{20-33}$ | RAVPGGSSPAWTQC | 100 | − |
| p6059 | 4 | $p19_{42-59}$ | C-TLAWSAHPLVGHMDLREE | 3000 | + |
| p6294 | 5 | $p19_{46-59}$ | C-SAHPLVGHMDLREE | 1000 | − |
| p7457 | 6 | $p19_{51-72}$ | C-VGHMDLREEGDEETTNDVPHIQ | 300 | − |
| p7458 | 7 | $p19_{51-72}$ | VGHMDLREEGDEETTNDVPHIQ-C | 300 | − |
| p7459 | 8 | $p19_{90-110}$ | C-LQRIHQGLIFYEKLLGSDIFT | 1000 | − |
| p7460 | 9 | $p19_{90-110}$ | LQRIHQGLIFYEKLLGSDIFT-C | 300 | − |
| p6061 | 10 | $p19_{100-119}$ | C-YEKLLGSDIFTGEPSLLPDS | 3000 | + |
| p6060 | 11 | $p19_{100-129}$ | C-YEKLLGSDIFTGEPSLLPDSPVGQLHASLL | 1000 | − |
| p6291 | 12 | $p19_{105-121}$ | C-GSDIFTGEPSLLPDSPV | 1000 | − |
| p6062 | 13 | $p19_{121-135}$ | C-VGQLHASLLGLSQLL | 100 | − |
| p7461 | 14 | $p19_{130-149}$ | C-GLSQLLQPEGHHWETQQIPS | 1000 | − |
| p7462 | 15 | $p19_{130-149}$ | GLSQLLQPEGHHWETQQIPS-C | 1000 | − |
| p6063 | 16 | $p19_{139-159}$ | C-GHHWETQQIPSLSPSQPWQRL | 300 | ++ |
| p7463 | 17 | $P19_{167-188}$ | C-RSLQAFVAVAARVFAHGAATLS | <100 | − |
| p7464 | 18 | $p19_{167-188}$ | RSLQAFVAVAARVFAHGAATLS-C | <100 | − |
| p6449 | 44 | $p40_{35-49}$ | C-LDWYPDAPGEMVVLT | 3000 | + |

[1] n is the dilution-factor in a α-IL23 ELISA at which oDmax/2 is reached.
[2] Functional relevance denotes the ability of a given serum to inhibit functional activity of rhuIL-23 as tested by splenocyte or STAT3p-assay.
−: no response, +: response, ++: strong response

TABLE 2

Strong MHC Class I binders within the sequence of p9269 and p8322 as defined by SYFPEITHI.

| No | Allele | Sequence | Score | Frequency | Population |
|---|---|---|---|---|---|
| 1 | HLA-A26 | E T Q Q I P S L S | 21 | 0-13% | Cuba |
| 2 |  | E T Q Q I P S L S P | 20 |  |  |
| 3 | HLA-B18* | W E T Q Q I P S L | 20 | 0-16% | Balkans |
| 4 | HLA-B37* | W E T Q Q I P S L | 24 | 0-7% | Belgium |
| 5 | HLA-B40: 01* | W E T Q Q I P S L | 20 | 0-28% | HK Chinese |
| 6 | HLA-B44: 02* | P E G H H W E T Q Q I | 20 | 0-25% | Ireland |
| 7 |  | W E T Q Q I P S L | 23 |  |  |

"Allele" describes the MHCI-Allele to which the respective sequence binds. An empty space in this column indicates that the allele is the same as in the line above.
"Sequence" shows the amino acid sequence of the predicted binder. Bold letters indicate primary anchor positions, underlined letters indicate secondary anchors.
"Score" represents the score calculated by SYFPEITHI. Higher scores indicate a higher probability to be a strong MHC class I binder.
"Frequency" denotes the frequency of a given allele in different human geographical and/or ethnical populations.
"Population" shows the geographical region and/or ethnicity, in which the highest frequency of a given allele occurs.
"Frequency" and "Population" are retrieved from an allele frequencies database.

From this disclosure, the following preferred embodiments are defined:

1. Vaccine for use in the prevention or treatment of an interleukin 23 (IL-23) related disease, comprising a peptide bound to a pharmaceutically acceptable carrier, wherein said peptide is selected from the group QPEGHHWETQQIPSLS (SEQ ID No. 103; p8322), GHHWETQQIPSLSPSQP-WQRL (SEQ ID No. 97; p6063), QPEGHHWETQ (SEQ ID No. 98; p8461), TQQIPSLSPSQ (SEQ ID No. 99; p8400), QPEGHHWETQQIPSLSPSQ (SEQ ID No. 100; p9269), QPEGHHWETQQIPSLSPS (SEQ ID No. 101; p9440), and QPEGHHWETQQIPSLSP (SEQ ID No. 102; p9441), especially QPEGHHWETQQIPSLS (SEQ ID No. 103; p8322) and wherein said IL-23 related disease is preferably selected from the group psoriasis, psoriatic arthritis, rheumatoid arthritis, systemic lupus erythematosus, diabetes, especially type 1 diabetes; atherosclerosis, inflammatory bowel disease (IBD)/M. Crohn, multiple sclerosis, Behçet disease, ankylosing spondylitis, Vogt-Koyanagi-Harada disease, chronic granulomatous disease, hidratenitis suppurtiva, anti-neutrophil cytoplasmic antibodies (ANCA-) associated vasculitides, neurodegenerative diseases, especially M. Alzheimer or multiple sclerosis; atopic dermatitis, graft-versus-host disease, cancer, especially Oesophagal carcinoma, colorectal carcinoma, lung adenocarcinoma, small cell carcinoma, and squamous cell carcinoma of the oral cavity; especially psoriasis, neurodegenerative diseases or IBD.

2. Vaccine according to embodiment 1, wherein at least one cysteine residue is bound to the N- or C-terminus of the peptide.

3. Vaccine according to embodiment 1 or 2, wherein at least one cysteine residue is bound to the N-terminus of the peptide.

4. Vaccine according to any one of embodiments 1 to 3, wherein the carrier is a protein carrier.

5. Vaccine according to embodiment 4, wherein the protein carrier is selected from the group consisting of keyhole limpet haemocyanin (KLH), tetanus toxoid (TT) or diphtheria toxin (DT).

6. Vaccine according to any one of embodiments 1 to 5, wherein the vaccine is formulated with an adjuvant, preferably wherein the peptide bound to the carrier is adsorbed to alum.

7. Vaccine according to any one of embodiments 1 to 6, formulated for intravenous, subcutaneous, intradermal or intramuscular administration.

8. Vaccine according to any one of embodiments 1 to 7, wherein the peptide is contained in the vaccine in an amount from 0.1 ng to 10 mg, preferably 10 ng to 1 mg, in particular 100 ng to 100 μg.

9. Vaccine according to any one of embodiments 1 to 8, wherein the peptide is bound to the carrier by a linker, preferably a peptide linker, especially a peptide linker having from 2 to 5 amino acid residues.

10. Vaccine according to embodiment 9, wherein the peptide linker is selected from the group Gly-Gly-Cys, Gly-Cys, Cys-Gly and Cys-Gly-Gly.

11. Vaccine according to any one of embodiments 1 to 10, wherein the vaccine is a biepitopic vaccine, especially a vaccine comprising a peptide of the group QPEGHHWETQQIPSLSPSQ (SEQ ID No. 100; p9269), QPEGHHWETQQIPSLSPS (SEQ ID No. 101; p9440), QPEGHHWETQQIPSLSP (SEQ ID No. 102; p9441), and QPEGHHWETQQIPSLS (SEQ ID No. 103; p8322).

12. Vaccine according to any one of embodiments 1 to 11, wherein the vaccine is a binary vaccine, especially a vaccine comprising a peptide from the group QPEGHHWETQQIPS (SEQ ID No. 104; p8495), QPEGHHWETQQIP (SEQ ID No. 105; p8459-1), QPEGHHWETQQI (SEQ ID No. 106; p8460), QPEGHHWETQQ (SEQ ID No. 107; P8460-1), QPEGHHWETQ (SEQ ID No. 98; p8461), QPEGHHWET (SEQ ID No. 108, p8461-1), QPEGHHWE (SEQ ID No. 109; p8462) and a peptide from the group TQQIPSLSPSQPWQ (SEQ ID No. 110, p8397), TQQIPSLSPSQPW (SEQ ID No. 111, p8398), TQQIPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), TQQIPSLS (SEQ ID No 115; p8763), preferably the peptide QPEGHHWETQ (SEQ ID No. 98; p8461) and the peptide TQQIPSLSPSQ (SEQ ID No. 99; p8400), each bound to a separate carrier.

13. Vaccine kit comprising a vaccine according to any one of embodiments 1 to 12 and a further vaccine addressing the Th17/IL-23 pathway, preferably an anti-IL-23 vaccine, especially an anti-p19-IL-23 vaccine.

14. Peptide, selected from the group GHHWETQQIPSLSPSQPWQRL (SEQ ID No. 97; p6063), QPEGHHWETQ (SEQ ID No. 98; p8461), TQQIPSLSPSQ (SEQ ID No. 99; p8400), QPEGHHWETQQIPSLSPSQ (SEQ ID No. 100; p9269), QPEGHHWETQQIPSLSPS (SEQ ID No. 101; p9440), QPEGHHWETQQIPSLSP (SEQ ID No. 102; p9441), QPEGHHWETQQIPSLS (SEQ ID No. 103; p8322), QPEGHHWETQQIPS (SEQ ID No. 104; p8495), QPEGHHWETQQIP (SEQ ID No. 105; p8459-1), QPEGHHWETQQI (SEQ ID No. 106; p8460), QPEGHHWETQQ (SEQ ID No. 107; p8460-1), QPEGHHWETQ (SEQ ID No. 98; p8461), QPEGHHWET (SEQ ID No. 108, p8461-1), QPEGHHWE (SEQ ID No. 109; p8462), TQQIPSLSPSQPWQ (SEQ ID No. 110, p8397), TQQIPSLSPSQPW (SEQ ID No. 111, p8398), TQQIPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), and TQQIPSLS (SEQ ID No 115; p8763).

15. Peptide pair, wherein one peptide is selected from the group QPEGHHWETQQIPS (SEQ ID No. 104; p8495), QPEGHHWETQQIP (SEQ ID No. 105; p8459-1), QPEGHHWETQQI (SEQ ID No. 106; p8460), QPEGHHWETQQ (SEQ ID No. 107; p8460-1), QPEGHHWETQ (SEQ ID No. 98; p8461), QPEGHHWET (SEQ ID No. 108, p8461-1), QPEGHHWE (SEQ ID No. 109; p8462) and the second peptide is selected from the group TQQIPSLSPSQPWQ (SEQ ID No. 110, p8397), TQQIPSLSPSQPW (SEQ ID No. 111, p8398), TQQIPSLSPSQP (SEQ ID No. 112, p8399), TQQIPSLSPSQ (SEQ ID No. 99; p8400), TQQIPSLSPS (SEQ ID No. 113; p8761), TQQIPSLSP (SEQ ID No. 114; p8762), TQQIPSLS (SEQ ID No 115; p8763), preferably the peptide QPEGHHWETQ (SEQ ID No. 98; p8461) and the peptide TQQIPSLSPSQ (SEQ ID No. 99; p8400).

REFERENCES

Aggarwal, S., Ghilardi, N., Xie, M. H., de Sauvage, F. J., and Gurney, A. L. (2003). Interleukin-23 promotes a distinct CD4 T cell activation state characterized by the production of interleukin-17. J Biol Chem 278, 1910-1914.

Brennan, F. M. & McInnes, I. B., Evidence that cytokines play a role in rheumatoid arthritis. J Clin Invest 118 (11), 3537-3545 (2008).

Chi, W. et al., Upregulated IL-23 and IL-17 in Behcet patients with active uveitis. Invest Ophthalmol Vis Sci 49 (7), 3058-3064 (2008).

Chi, W. et al., IL-23 promotes CD4 T cells to produce IL-17 in Vogt-Koyanagi-Harada disease. J Allergy Clin Immunol 119 (5), 1218-1224 (2007).

Cingoz, O. (2009). Ustekinumab. MAbs 1, 216-221.

Gaffen, S. L., Jain, R., Garg, A. V., and Cua, D. J. (2014). The IL-23-IL-17 immune axis: from mechanisms to therapeutic testing. Nat Rev Immunol 14, 585-600.

Fukuda, M., Ehara, M., Suzuki, S., Ohmori, Y., & Sakashita, H., IL-23 promotes growth and proliferation in human squamous cell carcinoma of the oral cavity. Int J Oncol 36 (6), 1355-1365 (2010).

Krutzik, P. O., and Nolan, G. P. (2003). Intracellular phospho-protein staining techniques for flow cytometry: monitoring single cell signaling events. Cytometry A 55, 61-70.

Lee, E., Trepicchio, W. L., Oestreicher, J. L., Pittman, D., Wang, F., Chamian, F., Dhodapkar, M., and Krueger, J. G. (2004). Increased expression of interleukin 23 p19 and p40 in lesional skin of patients with psoriasis vulgaris. J Exp Med 199, 125-130.

Leng, R. X. et al., IL-23: a promising therapeutic target for systemic lupus erythematosus. Arch Med Res 41 (3), 221-225 (2010).

Monteleone, I., Pallone, F., & Monteleone, G., Interleukin-23 and Th17 cells in the control of gut inflammation. Mediators Inflamm 2009, 297645 (2009).

Nestle, F. O., Kaplan, D. H., and Barker, J. (2009). Psoriasis. N Engl J Med 361, 496-509.

O'Hagan, D. T., and Valiante, N. M. (2003). Recent advances in the discovery and delivery of vaccine adjuvants. Nat Rev Drug Discov 2, 727-735.

Oppmann, B., Lesley, R., Blom, B., Timans, J. C., Xu, Y., Hunte, B., Vega, F., Yu, N., Wang, J., Singh, K., et al. (2000). Novel p19 protein engages IL-12p40 to form a cytokine, IL-23, with biological activities similar as well as distinct from IL-12. Immunity 13, 715-725.

Ratsimandresy, R. A., Duvallet, E., Assier, E., Semerano, L., Delavallee, L., Bessis, N., Zagury, J. F., and Boissier, M. C. (2011). Active immunization against IL-23p19 improves experimental arthritis. Vaccine 29, 9329-9336.

Schlapbach, C., Hänni, T., Yawalkar, N., & Hunger, R. E., Expression of the IL-23/Th17 pathway in lesions of hidradenitis suppurativa. J Am Acad Dermatol 65 (4), 790-798 (2011).

Sjölander, A., Cox, J. C., and Barr, I. G. (1998). ISCOMs: an adjuvant with multiple functions. J Leukoc Biol 64, 713-723.

Sonderegger, I., Rohn, T. A., Kurrer, M. O., Iezzi, G., Zou, Y., Kastelein, R. A., Bachmann, M. F., and Kopf, M. (2006). Neutralization of IL-17 by active vaccination inhibits IL-23-dependent autoimmune myocarditis. Eur J Immunol 36, 2849-2856.

Uchida, T., Pappenheimer, A. M., Jr., and Greany, R. (1973). Diphtheria toxin and related proteins. I. Isolation and properties of mutant proteins serologically related to diphtheria toxin. J Biol Chem 248, 3838-3844.

Uyttenhove, C., Arendse, B., Stroobant, V., Brombacher, F., and Van Snick, J. (2004). Development of an anti-IL-12 p40 auto-vaccine: protection in experimental autoimmune encephalomyelitis at the expense of increased sensitivity to infection. Eur J Immunol 34, 3572-3581.

Vom Berg, J. et al., Inhibition of IL-12/IL-23 signaling reduces Alzheimer's disease-like pathology and cognitive decline. Nat Med 18 (12), 1812-1819 (2012).

Wippel-Slupetzky, K., and Stingl, G. (2009). Future Perspectives in the Treatment of Psoriasis. Curr Probl Dermatol 38, 172-189.

Zeng, L., Lindstrom, M. J., & Smith, J. A., Ankylosing spondylitis macrophage production of higher levels of interleukin-23 in response to lipopolysaccharide without induction of a significant unfolded protein response. Arthritis Rheum 63 (12), 3807-3817 (2011).

The invention claimed is:

1. A composition, comprising:
   two peptides, each separately bound to a pharmaceutically acceptable carrier, wherein the two peptides are selected from the group consisting of SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, and SEQ ID NO: 115).

2. The composition according to claim 1, wherein at least one cysteine residue is bound to an N- or C-terminus of at least one of the peptides.

3. The composition according to claim 1, wherein at least one cysteine residue is bound to an N-terminus of at least one the peptides.

4. The composition according to claim 1, wherein the pharmaceutically acceptable carrier is a protein carrier.

5. The composition according to claim 4, wherein the protein carrier is selected from the group consisting of keyhole limpet haemocyanin, tetanus toxoid and diphtheria toxin.

6. The composition according to claim 1, wherein the composition is formulated with an adjuvant.

7. The composition according to claim 1, wherein the peptides are contained in the composition in an amount from 0.1 ng to 10 mg.

8. The composition according to claim 1, wherein the peptides are bound to the pharmaceutically acceptable carrier by a linker.

9. The composition according to claim 8, wherein the peptides are bound to the pharmaceutically acceptable carrier by a peptide linker and the peptide linker is selected from the group consisting of Gly-Gly-Cys, Gly-Cys, Cys-Gly and Cys- Gly-Gly.

10. The composition according to claim 1, wherein the composition is a biepitopic vaccine.

11. The composition according to claim 10, wherein the biepitopic vaccine comprises a peptide selected from the group consisting of SEQ ID NO: 100; SEQ ID NO: 101; SEQ ID NO: 102; SEQ ID NO: 103.

12. The composition according to claim 1, wherein at least one of the peptides is selected from the group consisting of SEQ ID NO: 103; SEQ ID NO: 98; SEQ ID NO: 99; SEQ ID NO: 100; SEQ ID NO: 101; and SEQ ID NO: 102.

13. A peptide pair, comprising:
   a first peptide selected from the group consisting of SEQ ID NO: 104; SEQ ID NO: 105; SEQ ID NO: 106; SEQ ID NO: 107; SEQ ID NO: 98; SEQ ID NO: 108, and SEQ ID NO: 109; and
   a second peptide selected from the group consisting of SEQ ID NO: 110, SEQ ID NO: 111, SEQ ID NO: 112, SEQ ID NO: 99; SEQ ID NO: 113; SEQ ID NO: 114; and SEQ ID NO: 115.

* * * * *

SEQUENCE LISTING

<160> NUMBER OF SEQ ID NOS: 141

<210> SEQ ID NO 1
<211> LENGTH: 189
<212> TYPE: PRT
<213> ORGANISM: Homo sapiens

<400> SEQUENCE: 1

```
Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 2
<211> LENGTH: 328
<212> TYPE: PRT
<213> ORGANISM: Homo sapiens

<400> SEQUENCE: 2

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 3
<211> LENGTH: 14
<212> TYPE: PRT
<213> ORGANISM: Homo sapiens

<400> SEQUENCE: 3

Arg Ala Val Pro Gly Gly Ser Ser Pro Ala Trp Thr Gln Cys
1               5                   10

<210> SEQ ID NO 4
<211> LENGTH: 19
<212> TYPE: PRT
<213> ORGANISM: Homo sapiens

<400> SEQUENCE: 4

Cys Thr Leu Ala Trp Ser Ala His Pro Leu Val Gly His Met Asp Leu
1               5                   10                  15

Arg Glu Glu

<210> SEQ ID NO 5
<211> LENGTH: 15
<212> TYPE: PRT
<213> ORGANISM: Homo sapiens

<400> SEQUENCE: 5

Cys Ser Ala His Pro Leu Val Gly His Met Asp Leu Arg Glu Glu
1               5                   10                  15

<210> SEQ ID NO 6
<211> LENGTH: 23
<212> TYPE: PRT
<213> ORGANISM: Homo sapiens

<400> SEQUENCE: 6

Cys Val Gly His Met Asp Leu Arg Glu Glu Gly Asp Glu Glu Thr Thr
1               5                   10                  15

Asn Asp Val Pro His Ile Gln
                20

<210> SEQ ID NO 7
<211> LENGTH: 23
<212> TYPE: PRT
<213> ORGANISM: Homo sapiens

<400> SEQUENCE: 7

Val Gly His Met Asp Leu Arg Glu Glu Gly Asp Glu Glu Thr Thr Asn
1               5                   10                  15

Asp Val Pro His Ile Gln Cys
                20

<210> SEQ ID NO 8
<211> LENGTH: 22
<212> TYPE: PRT
<213> ORGANISM: Homo sapiens

<400> SEQUENCE: 8

Cys Leu Gln Arg Ile His Gln Gly Leu Ile Phe Tyr Glu Lys Leu Leu
1               5                   10                  15

Gly Ser Asp Ile Phe Thr
                20

<210> SEQ ID NO 9
<211> LENGTH: 22
<212> TYPE: PRT
<213> ORGANISM: Homo sapiens

<400> SEQUENCE: 9

Leu Gln Arg Ile His Gln Gly Leu Ile Phe Tyr Glu Lys Leu Leu Gly

```
Ser Asp Ile Phe Thr Cys
            20

<210> SEQ ID NO 10
<211> LENGTH: 21
<212> TYPE: PRT
<213> ORGANISM: Homo sapiens

<400> SEQUENCE: 10

Cys Tyr Glu Lys Leu Leu Gly Ser Asp Ile Phe Thr Gly Glu Pro Ser
1               5                   10                  15

Leu Leu Pro Asp Ser
            20

<210> SEQ ID NO 11
<211> LENGTH: 31
<212> TYPE: PRT
<213> ORGANISM: Homo sapiens

<400> SEQUENCE: 11

Cys Tyr Glu Lys Leu Leu Gly Ser Asp Ile Phe Thr Gly Glu Pro Ser
1               5                   10                  15

Leu Leu Pro Asp Ser Pro Val Gly Gln Leu His Ala Ser Leu Leu
            20                  25                  30

<210> SEQ ID NO 12
<211> LENGTH: 18
<212> TYPE: PRT
<213> ORGANISM: Homo sapiens

<400> SEQUENCE: 12

Cys Gly Ser Asp Ile Phe Thr Gly Glu Pro Ser Leu Leu Pro Asp Ser
1               5                   10                  15

Pro Val

<210> SEQ ID NO 13
<211> LENGTH: 16
<212> TYPE: PRT
<213> ORGANISM: Homo sapiens

<400> SEQUENCE: 13

Cys Val Gly Gln Leu His Ala Ser Leu Leu Gly Leu Ser Gln Leu Leu
1               5                   10                  15

<210> SEQ ID NO 14
<211> LENGTH: 21
<212> TYPE: PRT
<213> ORGANISM: Homo sapiens

<400> SEQUENCE: 14

Cys Gly Leu Ser Gln Leu Leu Gln Pro Glu Gly His His Trp Glu Thr
1               5                   10                  15

Gln Gln Ile Pro Ser
            20

<210> SEQ ID NO 15
<211> LENGTH: 21
<212> TYPE: PRT
<213> ORGANISM: Homo sapiens

<400> SEQUENCE: 15
```

```
Gly Leu Ser Gln Leu Leu Gln Pro Glu Gly His His Trp Glu Thr Gln
1               5                   10                  15

Gln Ile Pro Ser Cys
            20
```

<210> SEQ ID NO 16
<211> LENGTH: 22
<212> TYPE: PRT
<213> ORGANISM: Homo sapiens

<400> SEQUENCE: 16

```
Cys Gly His His Trp Glu Thr Gln Gln Ile Pro Ser Leu Ser Pro Ser
1               5                   10                  15

Gln Pro Trp Gln Arg Leu
            20
```

<210> SEQ ID NO 17
<211> LENGTH: 23
<212> TYPE: PRT
<213> ORGANISM: Homo sapiens

<400> SEQUENCE: 17

```
Cys Arg Ser Leu Gln Ala Phe Val Ala Val Ala Ala Arg Val Phe Ala
1               5                   10                  15

His Gly Ala Ala Thr Leu Ser
            20
```

<210> SEQ ID NO 18
<211> LENGTH: 23
<212> TYPE: PRT
<213> ORGANISM: Homo sapiens

<400> SEQUENCE: 18

```
Arg Ser Leu Gln Ala Phe Val Ala Val Ala Ala Arg Val Phe Ala His
1               5                   10                  15

Gly Ala Ala Thr Leu Ser Cys
            20
```

<210> SEQ ID NO 19
<211> LENGTH: 16
<212> TYPE: PRT
<213> ORGANISM: Homo sapiens

<400> SEQUENCE: 19

```
Cys Thr Gln Gln Ile Pro Ser Leu Ser Pro Ser Gln Pro Trp Gln Arg
1               5                   10                  15
```

<210> SEQ ID NO 20
<211> LENGTH: 9
<212> TYPE: PRT
<213> ORGANISM: Homo sapiens

<400> SEQUENCE: 20

```
Cys His His Trp Glu Thr Gln Gln Ile
1               5
```

<210> SEQ ID NO 21
<211> LENGTH: 22
<212> TYPE: PRT
<213> ORGANISM: Homo sapiens

<400> SEQUENCE: 21

```
Cys Glu Gly His His Trp Glu Thr Gln Gln Ile Pro Ser Leu Ser Pro
```

```
1               5                   10                  15

Ser Gln Pro Trp Gln Arg
            20

<210> SEQ ID NO 22
<211> LENGTH: 21
<212> TYPE: PRT
<213> ORGANISM: Homo sapiens

<400> SEQUENCE: 22

Cys Ser Gln Leu Leu Gln Pro Glu Gly His His Trp Glu Thr Gln Gln
1               5                   10                  15

Ile Pro Ser Leu Ser
            20

<210> SEQ ID NO 23
<211> LENGTH: 19
<212> TYPE: PRT
<213> ORGANISM: Homo sapiens

<400> SEQUENCE: 23

Cys Leu Leu Gln Pro Glu Gly His His Trp Glu Thr Gln Gln Ile Pro
1               5                   10                  15

Ser Leu Ser

<210> SEQ ID NO 24
<211> LENGTH: 17
<212> TYPE: PRT
<213> ORGANISM: Homo sapiens

<400> SEQUENCE: 24

Cys Gln Pro Glu Gly His His Trp Glu Thr Gln Gln Ile Pro Ser Leu
1               5                   10                  15

Ser

<210> SEQ ID NO 25
<211> LENGTH: 17
<212> TYPE: PRT
<213> ORGANISM: Homo sapiens

<400> SEQUENCE: 25

Cys Gln Pro Glu Gly His His Trp Glu Thr Gln Gln Ile Pro Ser Leu
1               5                   10                  15

Ser

<210> SEQ ID NO 26
<211> LENGTH: 15
<212> TYPE: PRT
<213> ORGANISM: Homo sapiens

<400> SEQUENCE: 26

Cys Gln Pro Glu Gly His His Trp Glu Thr Gln Gln Ile Pro Ser
1               5                   10                  15

<210> SEQ ID NO 27
<211> LENGTH: 13
<212> TYPE: PRT
<213> ORGANISM: Homo sapiens

<400> SEQUENCE: 27

Cys Gln Pro Glu Gly His His Trp Glu Thr Gln Gln Ile
1               5                   10
```

<210> SEQ ID NO 28
<211> LENGTH: 11
<212> TYPE: PRT
<213> ORGANISM: Homo sapiens

<400> SEQUENCE: 28

Cys Gln Pro Glu Gly His His Trp Glu Thr Gln
1               5                   10

<210> SEQ ID NO 29
<211> LENGTH: 9
<212> TYPE: PRT
<213> ORGANISM: Homo sapiens

<400> SEQUENCE: 29

Cys Gln Pro Glu Gly His His Trp Glu
1               5

<210> SEQ ID NO 30
<211> LENGTH: 15
<212> TYPE: PRT
<213> ORGANISM: Homo sapiens

<400> SEQUENCE: 30

Cys Thr Gln Gln Ile Pro Ser Leu Ser Pro Ser Gln Pro Trp Gln
1               5                   10                  15

<210> SEQ ID NO 31
<211> LENGTH: 14
<212> TYPE: PRT
<213> ORGANISM: Homo sapiens

<400> SEQUENCE: 31

Cys Thr Gln Gln Ile Pro Ser Leu Ser Pro Ser Gln Pro Trp
1               5                   10

<210> SEQ ID NO 32
<211> LENGTH: 13
<212> TYPE: PRT
<213> ORGANISM: Homo sapiens

<400> SEQUENCE: 32

Cys Thr Gln Gln Ile Pro Ser Leu Ser Pro Ser Gln Pro
1               5                   10

<210> SEQ ID NO 33
<211> LENGTH: 12
<212> TYPE: PRT
<213> ORGANISM: Homo sapiens

<400> SEQUENCE: 33

Cys Thr Gln Gln Ile Pro Ser Leu Ser Pro Ser Gln
1               5                   10

<210> SEQ ID NO 34
<211> LENGTH: 11
<212> TYPE: PRT
<213> ORGANISM: Homo sapiens

<400> SEQUENCE: 34

Cys Thr Gln Gln Ile Pro Ser Leu Ser Pro Ser
1               5                   10

```
<210> SEQ ID NO 35
<211> LENGTH: 10
<212> TYPE: PRT
<213> ORGANISM: Homo sapiens

<400> SEQUENCE: 35

Cys Thr Gln Gln Ile Pro Ser Leu Ser Pro
1               5                   10

<210> SEQ ID NO 36
<211> LENGTH: 9
<212> TYPE: PRT
<213> ORGANISM: Homo sapiens

<400> SEQUENCE: 36

Cys Thr Gln Gln Ile Pro Ser Leu Ser
1               5

<210> SEQ ID NO 37
<211> LENGTH: 11
<212> TYPE: PRT
<213> ORGANISM: Homo sapiens

<400> SEQUENCE: 37

Cys Pro Glu Gly His His Trp Glu Thr Gln Gln
1               5                   10

<210> SEQ ID NO 38
<211> LENGTH: 11
<212> TYPE: PRT
<213> ORGANISM: Homo sapiens

<400> SEQUENCE: 38

Cys Pro Trp Gln Arg Leu Leu Leu Arg Phe Lys
1               5                   10

<210> SEQ ID NO 39
<211> LENGTH: 12
<212> TYPE: PRT
<213> ORGANISM: Homo sapiens

<400> SEQUENCE: 39

Cys Ser Leu Leu Gly Leu Ser Gln Leu Leu Gln Pro
1               5                   10

<210> SEQ ID NO 40
<211> LENGTH: 20
<212> TYPE: PRT
<213> ORGANISM: Homo sapiens

<400> SEQUENCE: 40

Cys Pro Glu Gly His His Trp Glu Thr Gln Gln Ile Pro Ser Leu Ser
1               5                   10                  15

Pro Ser Gln Pro
            20

<210> SEQ ID NO 41
<211> LENGTH: 21
<212> TYPE: PRT
<213> ORGANISM: Homo sapiens

<400> SEQUENCE: 41

Cys Leu Leu Arg Phe Lys Ile Leu Arg Ser Leu Gln Ala Phe Val Ala
1               5                   10                  15
```

```
Val Ala Ala Arg Val
            20

<210> SEQ ID NO 42
<211> LENGTH: 9
<212> TYPE: PRT
<213> ORGANISM: Homo sapiens

<400> SEQUENCE: 42

Cys Pro Ser Gln Pro Trp Gln Arg Leu
1               5

<210> SEQ ID NO 43
<211> LENGTH: 20
<212> TYPE: PRT
<213> ORGANISM: Homo sapiens

<400> SEQUENCE: 43

Cys Gln Pro Glu Gly His His Trp Glu Thr Gln Gln Ile Pro Ser Leu
1               5                   10                  15

Ser Pro Ser Gln
            20

<210> SEQ ID NO 44
<211> LENGTH: 16
<212> TYPE: PRT
<213> ORGANISM: Homo sapiens

<400> SEQUENCE: 44

Cys Leu Asp Trp Tyr Pro Asp Ala Pro Gly Glu Met Val Val Leu Thr
1               5                   10                  15

<210> SEQ ID NO 45
<211> LENGTH: 20
<212> TYPE: PRT
<213> ORGANISM: Homo sapiens

<400> SEQUENCE: 45

Cys Val Val Ala Ser Gln Leu Arg Ala Asn Ile Ser His Lys Asp Met
1               5                   10                  15

Gln Leu Gly Arg
            20

<210> SEQ ID NO 46
<211> LENGTH: 19
<212> TYPE: PRT
<213> ORGANISM: Homo sapiens

<400> SEQUENCE: 46

Cys Gln Pro Glu Gly His His Trp Glu Thr Gln Gln Ile Pro Ser Leu
1               5                   10                  15

Ser Pro Ser

<210> SEQ ID NO 47
<211> LENGTH: 18
<212> TYPE: PRT
<213> ORGANISM: Homo sapiens

<400> SEQUENCE: 47

Cys Gln Pro Glu Gly His His Trp Glu Thr Gln Gln Ile Pro Ser Leu
1               5                   10                  15

Ser Pro
```

```
<210> SEQ ID NO 48
<211> LENGTH: 9
<212> TYPE: PRT
<213> ORGANISM: Homo sapiens

<400> SEQUENCE: 48

Glu Thr Gln Gln Ile Pro Ser Leu Ser
1               5

<210> SEQ ID NO 49
<211> LENGTH: 9
<212> TYPE: PRT
<213> ORGANISM: Homo sapiens

<400> SEQUENCE: 49

Glu Thr Gln Gln Ile Pro Ser Leu Ser
1               5

<210> SEQ ID NO 50
<211> LENGTH: 9
<212> TYPE: PRT
<213> ORGANISM: Homo sapiens

<400> SEQUENCE: 50

Trp Glu Thr Gln Gln Ile Pro Ser Leu
1               5

<210> SEQ ID NO 51
<211> LENGTH: 11
<212> TYPE: PRT
<213> ORGANISM: Homo sapiens

<400> SEQUENCE: 51

Pro Glu Gly His His Trp Glu Thr Gln Gln Ile
1               5                   10

<210> SEQ ID NO 52
<211> LENGTH: 65
<212> TYPE: PRT
<213> ORGANISM: Homo sapiens

<400> SEQUENCE: 52

Gly Ser Gly Ser Gly Ser Gly Leu His Ala Ser Leu Leu Gly Leu Ser
1               5                   10                  15

Gln Leu Leu Gln Pro Glu Gly His His Trp Glu Thr Gln Gln Ile Pro
            20                  25                  30

Ser Leu Ser Pro Ser Gln Pro Trp Gln Arg Leu Leu Leu Arg Phe Lys
        35                  40                  45

Ile Leu Arg Ser Leu Gln Ala Phe Val Ala Gly Ser Gly Ser Gly Ser
    50                  55                  60

Gly
65

<210> SEQ ID NO 53
<211> LENGTH: 55
<212> TYPE: PRT
<213> ORGANISM: Homo sapiens

<400> SEQUENCE: 53

His Ala Ser Leu Leu Gly Leu Ser Gln Leu Leu Gln Pro Glu Gly His
1               5                   10                  15

His Trp Glu Thr Gln Gln Ile Pro Ser Leu Ser Pro Ser Gln Pro Trp
```

```
                20                  25                  30
Gln Arg Leu Leu Leu Arg Phe Lys Ile Leu Arg Ser Leu Gln Ala Phe
            35                  40                  45
Val Ala Val Ala Ala Arg Val
        50                  55

<210> SEQ ID NO 54
<211> LENGTH: 12
<212> TYPE: PRT
<213> ORGANISM: Homo sapiens

<400> SEQUENCE: 54

Ala Ser Leu Leu Gly Leu Ser Gln Leu Leu Gln Pro
1               5                   10

<210> SEQ ID NO 55
<211> LENGTH: 12
<212> TYPE: PRT
<213> ORGANISM: Homo sapiens

<400> SEQUENCE: 55

Ser Leu Leu Gly Leu Ser Gln Leu Leu Gln Pro Glu
1               5                   10

<210> SEQ ID NO 56
<211> LENGTH: 12
<212> TYPE: PRT
<213> ORGANISM: Homo sapiens

<400> SEQUENCE: 56

Leu Leu Gly Leu Ser Gln Leu Leu Gln Pro Glu Gly
1               5                   10

<210> SEQ ID NO 57
<211> LENGTH: 12
<212> TYPE: PRT
<213> ORGANISM: Homo sapiens

<400> SEQUENCE: 57

Leu Gly Leu Ser Gln Leu Leu Gln Pro Glu Gly His
1               5                   10

<210> SEQ ID NO 58
<211> LENGTH: 12
<212> TYPE: PRT
<213> ORGANISM: Homo sapiens

<400> SEQUENCE: 58

Gly Leu Ser Gln Leu Leu Gln Pro Glu Gly His His
1               5                   10

<210> SEQ ID NO 59
<211> LENGTH: 12
<212> TYPE: PRT
<213> ORGANISM: Homo sapiens

<400> SEQUENCE: 59

Leu Ser Gln Leu Leu Gln Pro Glu Gly His His Trp
1               5                   10

<210> SEQ ID NO 60
<211> LENGTH: 12
<212> TYPE: PRT
<213> ORGANISM: Homo sapiens
```

-continued

<400> SEQUENCE: 60

Ser Gln Leu Leu Gln Pro Glu Gly His His Trp Glu
1               5                   10

<210> SEQ ID NO 61
<211> LENGTH: 12
<212> TYPE: PRT
<213> ORGANISM: Homo sapiens

<400> SEQUENCE: 61

Gln Leu Leu Gln Pro Glu Gly His His Trp Glu Thr
1               5                   10

<210> SEQ ID NO 62
<211> LENGTH: 12
<212> TYPE: PRT
<213> ORGANISM: Homo sapiens

<400> SEQUENCE: 62

Leu Leu Gln Pro Glu Gly His His Trp Glu Thr Gln
1               5                   10

<210> SEQ ID NO 63
<211> LENGTH: 12
<212> TYPE: PRT
<213> ORGANISM: Homo sapiens

<400> SEQUENCE: 63

Leu Gln Pro Glu Gly His His Trp Glu Thr Gln Gln
1               5                   10

<210> SEQ ID NO 64
<211> LENGTH: 12
<212> TYPE: PRT
<213> ORGANISM: Homo sapiens

<400> SEQUENCE: 64

Gln Pro Glu Gly His His Trp Glu Thr Gln Gln Ile
1               5                   10

<210> SEQ ID NO 65
<211> LENGTH: 12
<212> TYPE: PRT
<213> ORGANISM: Homo sapiens

<400> SEQUENCE: 65

Pro Glu Gly His His Trp Glu Thr Gln Gln Ile Pro
1               5                   10

<210> SEQ ID NO 66
<211> LENGTH: 12
<212> TYPE: PRT
<213> ORGANISM: Homo sapiens

<400> SEQUENCE: 66

Glu Gly His His Trp Glu Thr Gln Gln Ile Pro Ser
1               5                   10

<210> SEQ ID NO 67
<211> LENGTH: 12
<212> TYPE: PRT
<213> ORGANISM: Homo sapiens

<400> SEQUENCE: 67

Gly His His Trp Glu Thr Gln Gln Ile Pro Ser Leu
1               5                   10

<210> SEQ ID NO 68
<211> LENGTH: 12
<212> TYPE: PRT
<213> ORGANISM: Homo sapiens

<400> SEQUENCE: 68

His His Trp Glu Thr Gln Gln Ile Pro Ser Leu Ser
1               5                   10

<210> SEQ ID NO 69
<211> LENGTH: 12
<212> TYPE: PRT
<213> ORGANISM: Homo sapiens

<400> SEQUENCE: 69

His Trp Glu Thr Gln Gln Ile Pro Ser Leu Ser Pro
1               5                   10

<210> SEQ ID NO 70
<211> LENGTH: 12
<212> TYPE: PRT
<213> ORGANISM: Homo sapiens

<400> SEQUENCE: 70

Trp Glu Thr Gln Gln Ile Pro Ser Leu Ser Pro Ser
1               5                   10

<210> SEQ ID NO 71
<211> LENGTH: 12
<212> TYPE: PRT
<213> ORGANISM: Homo sapiens

<400> SEQUENCE: 71

Glu Thr Gln Gln Ile Pro Ser Leu Ser Pro Ser Gln
1               5                   10

<210> SEQ ID NO 72
<211> LENGTH: 12
<212> TYPE: PRT
<213> ORGANISM: Homo sapiens

<400> SEQUENCE: 72

Thr Gln Gln Ile Pro Ser Leu Ser Pro Ser Gln Pro
1               5                   10

<210> SEQ ID NO 73
<211> LENGTH: 12
<212> TYPE: PRT
<213> ORGANISM: Homo sapiens

<400> SEQUENCE: 73

Gln Gln Ile Pro Ser Leu Ser Pro Ser Gln Pro Trp
1               5                   10

<210> SEQ ID NO 74
<211> LENGTH: 12
<212> TYPE: PRT
<213> ORGANISM: Homo sapiens

<400> SEQUENCE: 74

Gln Ile Pro Ser Leu Ser Pro Ser Gln Pro Trp Gln

-continued

```
<210> SEQ ID NO 75
<211> LENGTH: 12
<212> TYPE: PRT
<213> ORGANISM: Homo sapiens

<400> SEQUENCE: 75

Ile Pro Ser Leu Ser Pro Ser Gln Pro Trp Gln Arg
1               5                   10

<210> SEQ ID NO 76
<211> LENGTH: 12
<212> TYPE: PRT
<213> ORGANISM: Homo sapiens

<400> SEQUENCE: 76

Pro Ser Leu Ser Pro Ser Gln Pro Trp Gln Arg Leu
1               5                   10

<210> SEQ ID NO 77
<211> LENGTH: 12
<212> TYPE: PRT
<213> ORGANISM: Homo sapiens

<400> SEQUENCE: 77

Pro Ser Leu Ser Pro Ser Gln Pro Trp Gln Arg Leu
1               5                   10

<210> SEQ ID NO 78
<211> LENGTH: 12
<212> TYPE: PRT
<213> ORGANISM: Homo sapiens

<400> SEQUENCE: 78

Leu Ser Pro Ser Gln Pro Trp Gln Arg Leu Leu Leu
1               5                   10

<210> SEQ ID NO 79
<211> LENGTH: 12
<212> TYPE: PRT
<213> ORGANISM: Homo sapiens

<400> SEQUENCE: 79

Ser Pro Ser Gln Pro Trp Gln Arg Leu Leu Leu Arg
1               5                   10

<210> SEQ ID NO 80
<211> LENGTH: 12
<212> TYPE: PRT
<213> ORGANISM: Homo sapiens

<400> SEQUENCE: 80

Pro Ser Gln Pro Trp Gln Arg Leu Leu Leu Arg Phe
1               5                   10

<210> SEQ ID NO 81
<211> LENGTH: 12
<212> TYPE: PRT
<213> ORGANISM: Homo sapiens

<400> SEQUENCE: 81

Ser Gln Pro Trp Gln Arg Leu Leu Leu Arg Phe Lys
1               5                   10
```

<210> SEQ ID NO 82
<211> LENGTH: 12
<212> TYPE: PRT
<213> ORGANISM: Homo sapiens

<400> SEQUENCE: 82

Gln Pro Trp Gln Arg Leu Leu Leu Arg Phe Lys Ile
1               5                   10

<210> SEQ ID NO 83
<211> LENGTH: 6
<212> TYPE: PRT
<213> ORGANISM: Homo sapiens

<400> SEQUENCE: 83

Gln Pro Glu Gly His His
1               5

<210> SEQ ID NO 84
<211> LENGTH: 6
<212> TYPE: PRT
<213> ORGANISM: Homo sapiens

<400> SEQUENCE: 84

Pro Glu Gly His His Trp
1               5

<210> SEQ ID NO 85
<211> LENGTH: 6
<212> TYPE: PRT
<213> ORGANISM: Homo sapiens

<400> SEQUENCE: 85

Glu Gly His His Trp Glu
1               5

<210> SEQ ID NO 86
<211> LENGTH: 6
<212> TYPE: PRT
<213> ORGANISM: Homo sapiens

<400> SEQUENCE: 86

Gly His His Trp Glu Thr
1               5

<210> SEQ ID NO 87
<211> LENGTH: 6
<212> TYPE: PRT
<213> ORGANISM: Homo sapiens

<400> SEQUENCE: 87

His His Trp Glu Thr Gln
1               5

<210> SEQ ID NO 88
<211> LENGTH: 6
<212> TYPE: PRT
<213> ORGANISM: Homo sapiens

<400> SEQUENCE: 88

His Trp Glu Thr Gln Gln
1               5

<210> SEQ ID NO 89

```
<211> LENGTH: 6
<212> TYPE: PRT
<213> ORGANISM: Homo sapiens

<400> SEQUENCE: 89

Trp Glu Thr Gln Gln Ile
1               5

<210> SEQ ID NO 90
<211> LENGTH: 6
<212> TYPE: PRT
<213> ORGANISM: Homo sapiens

<400> SEQUENCE: 90

Glu Thr Gln Gln Ile Pro
1               5

<210> SEQ ID NO 91
<211> LENGTH: 6
<212> TYPE: PRT
<213> ORGANISM: Homo sapiens

<400> SEQUENCE: 91

Thr Gln Gln Ile Pro Ser
1               5

<210> SEQ ID NO 92
<211> LENGTH: 6
<212> TYPE: PRT
<213> ORGANISM: Homo sapiens

<400> SEQUENCE: 92

Gln Gln Ile Pro Ser Leu
1               5

<210> SEQ ID NO 93
<211> LENGTH: 6
<212> TYPE: PRT
<213> ORGANISM: Homo sapiens

<400> SEQUENCE: 93

Gln Ile Pro Ser Leu Ser
1               5

<210> SEQ ID NO 94
<211> LENGTH: 6
<212> TYPE: PRT
<213> ORGANISM: Homo sapiens

<400> SEQUENCE: 94

Ile Pro Ser Leu Ser Pro
1               5

<210> SEQ ID NO 95
<211> LENGTH: 6
<212> TYPE: PRT
<213> ORGANISM: Homo sapiens

<400> SEQUENCE: 95

Pro Ser Leu Ser Pro Ser
1               5

<210> SEQ ID NO 96
<211> LENGTH: 6
<212> TYPE: PRT
```

<213> ORGANISM: Homo sapiens

<400> SEQUENCE: 96

Ser Leu Ser Pro Ser Gln
1               5

<210> SEQ ID NO 97
<211> LENGTH: 21
<212> TYPE: PRT
<213> ORGANISM: Homo sapiens

<400> SEQUENCE: 97

Gly His His Trp Glu Thr Gln Gln Ile Pro Ser Leu Ser Pro Ser Gln
1               5                   10                  15

Pro Trp Gln Arg Leu
            20

<210> SEQ ID NO 98
<211> LENGTH: 10
<212> TYPE: PRT
<213> ORGANISM: Homo sapiens

<400> SEQUENCE: 98

Gln Pro Glu Gly His His Trp Glu Thr Gln
1               5                   10

<210> SEQ ID NO 99
<211> LENGTH: 11
<212> TYPE: PRT
<213> ORGANISM: Homo sapiens

<400> SEQUENCE: 99

Thr Gln Gln Ile Pro Ser Leu Ser Pro Ser Gln
1               5                   10

<210> SEQ ID NO 100
<211> LENGTH: 19
<212> TYPE: PRT
<213> ORGANISM: Homo sapiens

<400> SEQUENCE: 100

Gln Pro Glu Gly His His Trp Glu Thr Gln Gln Ile Pro Ser Leu Ser
1               5                   10                  15

Pro Ser Gln

<210> SEQ ID NO 101
<211> LENGTH: 18
<212> TYPE: PRT
<213> ORGANISM: Homo sapiens

<400> SEQUENCE: 101

Gln Pro Glu Gly His His Trp Glu Thr Gln Gln Ile Pro Ser Leu Ser
1               5                   10                  15

Pro Ser

<210> SEQ ID NO 102
<211> LENGTH: 17
<212> TYPE: PRT
<213> ORGANISM: Homo sapiens

<400> SEQUENCE: 102

Gln Pro Glu Gly His His Trp Glu Thr Gln Gln Ile Pro Ser Leu Ser
1               5                   10                  15

Pro

<210> SEQ ID NO 103
<211> LENGTH: 16
<212> TYPE: PRT
<213> ORGANISM: Homo sapiens

<400> SEQUENCE: 103

Gln Pro Glu Gly His His Trp Glu Thr Gln Gln Ile Pro Ser Leu Ser
1               5                   10                  15

<210> SEQ ID NO 104
<211> LENGTH: 14
<212> TYPE: PRT
<213> ORGANISM: Homo sapiens

<400> SEQUENCE: 104

Gln Pro Glu Gly His His Trp Glu Thr Gln Gln Ile Pro Ser
1               5                   10

<210> SEQ ID NO 105
<211> LENGTH: 13
<212> TYPE: PRT
<213> ORGANISM: Homo sapiens

<400> SEQUENCE: 105

Gln Pro Glu Gly His His Trp Glu Thr Gln Gln Ile Pro
1               5                   10

<210> SEQ ID NO 106
<211> LENGTH: 12
<212> TYPE: PRT
<213> ORGANISM: Homo sapiens

<400> SEQUENCE: 106

Gln Pro Glu Gly His His Trp Glu Thr Gln Gln Ile
1               5                   10

<210> SEQ ID NO 107
<211> LENGTH: 11
<212> TYPE: PRT
<213> ORGANISM: Homo sapiens

<400> SEQUENCE: 107

Gln Pro Glu Gly His His Trp Glu Thr Gln Gln
1               5                   10

<210> SEQ ID NO 108
<211> LENGTH: 9
<212> TYPE: PRT
<213> ORGANISM: Homo sapiens

<400> SEQUENCE: 108

Gln Pro Glu Gly His His Trp Glu Thr
1               5

<210> SEQ ID NO 109
<211> LENGTH: 8
<212> TYPE: PRT
<213> ORGANISM: Homo sapiens

<400> SEQUENCE: 109

Gln Pro Glu Gly His His Trp Glu
1               5

```
<210> SEQ ID NO 110
<211> LENGTH: 14
<212> TYPE: PRT
<213> ORGANISM: Homo sapiens

<400> SEQUENCE: 110

Thr Gln Gln Ile Pro Ser Leu Ser Pro Ser Gln Pro Trp Gln
1               5                   10

<210> SEQ ID NO 111
<211> LENGTH: 13
<212> TYPE: PRT
<213> ORGANISM: Homo sapiens

<400> SEQUENCE: 111

Thr Gln Gln Ile Pro Ser Leu Ser Pro Ser Gln Pro Trp
1               5                   10

<210> SEQ ID NO 112
<211> LENGTH: 12
<212> TYPE: PRT
<213> ORGANISM: Homo sapiens

<400> SEQUENCE: 112

Thr Gln Gln Ile Pro Ser Leu Ser Pro Ser Gln Pro
1               5                   10

<210> SEQ ID NO 113
<211> LENGTH: 10
<212> TYPE: PRT
<213> ORGANISM: Homo sapiens

<400> SEQUENCE: 113

Thr Gln Gln Ile Pro Ser Leu Ser Pro Ser
1               5                   10

<210> SEQ ID NO 114
<211> LENGTH: 9
<212> TYPE: PRT
<213> ORGANISM: Homo sapiens

<400> SEQUENCE: 114

Thr Gln Gln Ile Pro Ser Leu Ser Pro
1               5

<210> SEQ ID NO 115
<211> LENGTH: 8
<212> TYPE: PRT
<213> ORGANISM: Homo sapiens

<400> SEQUENCE: 115

Thr Gln Gln Ile Pro Ser Leu Ser
1               5

<210> SEQ ID NO 116
<211> LENGTH: 14
<212> TYPE: PRT
<213> ORGANISM: Homo sapiens

<400> SEQUENCE: 116

Phe Tyr Glu Lys Leu Leu Gly Ser Asp Ile Phe Thr Gly Glu
1               5                   10
```

```
<210> SEQ ID NO 117
<211> LENGTH: 22
<212> TYPE: PRT
<213> ORGANISM: Homo sapiens

<400> SEQUENCE: 117

Phe Tyr Glu Lys Leu Leu Gly Ser Asp Ile Phe Thr Gly Glu Pro Ser
1               5                   10                  15

Leu Leu Pro Asp Ser Pro
            20

<210> SEQ ID NO 118
<211> LENGTH: 17
<212> TYPE: PRT
<213> ORGANISM: Homo sapiens

<400> SEQUENCE: 118

Val Ala Gln Leu His Ala Ser Leu Leu Gly Leu Ser Gln Leu Leu Gln
1               5                   10                  15

Pro

<210> SEQ ID NO 119
<211> LENGTH: 27
<212> TYPE: PRT
<213> ORGANISM: Homo sapiens

<400> SEQUENCE: 119

Gly Glu Pro Ser Leu Leu Pro Asp Ser Pro Val Ala Gln Leu His Ala
1               5                   10                  15

Ser Leu Leu Gly Leu Ser Gln Leu Leu Gln Pro
            20                  25

<210> SEQ ID NO 120
<211> LENGTH: 19
<212> TYPE: PRT
<213> ORGANISM: Homo sapiens

<400> SEQUENCE: 120

Pro Glu Gly His His Trp Glu Thr Gln Gln Ile Pro Ser Leu Ser Pro
1               5                   10                  15

Ser Gln Pro

<210> SEQ ID NO 121
<211> LENGTH: 8
<212> TYPE: PRT
<213> ORGANISM: Homo sapiens

<400> SEQUENCE: 121

Pro Ser Leu Leu Pro Asp Ser Pro
1               5

<210> SEQ ID NO 122
<211> LENGTH: 7
<212> TYPE: PRT
<213> ORGANISM: Homo sapiens

<400> SEQUENCE: 122

Leu Pro Asp Ser Pro Val Ala
1               5

<210> SEQ ID NO 123
<211> LENGTH: 39
<212> TYPE: PRT
```

```
<213> ORGANISM: Homo sapiens

<400> SEQUENCE: 123

Phe Tyr Glu Lys Leu Leu Gly Ser Asp Ile Phe Thr Gly Glu Pro Ser
1               5                   10                  15

Leu Leu Pro Asp Ser Pro Val Ala Gln Leu His Ala Ser Leu Leu Gly
            20                  25                  30

Leu Ser Gln Leu Leu Gln Pro
        35

<210> SEQ ID NO 124
<211> LENGTH: 6
<212> TYPE: PRT
<213> ORGANISM: Homo sapiens

<400> SEQUENCE: 124

Leu Leu Pro Asp Ser Pro
1               5

<210> SEQ ID NO 125
<211> LENGTH: 28
<212> TYPE: PRT
<213> ORGANISM: Homo sapiens

<400> SEQUENCE: 125

Leu Leu Gly Ser Asp Ile Phe Thr Gly Glu Pro Ser Leu Leu Pro Asp
1               5                   10                  15

Ser Pro Val Ala Gln Leu His Ala Ser Leu Leu Gly
            20                  25

<210> SEQ ID NO 126
<211> LENGTH: 32
<212> TYPE: PRT
<213> ORGANISM: Homo sapiens

<400> SEQUENCE: 126

Phe Tyr Glu Lys Leu Leu Gly Ser Asp Ile Phe Thr Gly Glu Pro Ser
1               5                   10                  15

Leu Leu Pro Asp Ser Pro Val Ala Gln Leu His Ala Ser Leu Leu Gly
            20                  25                  30

<210> SEQ ID NO 127
<211> LENGTH: 7
<212> TYPE: PRT
<213> ORGANISM: Homo sapiens

<400> SEQUENCE: 127

Gln Pro Glu Gly His His Trp
1               5

<210> SEQ ID NO 128
<211> LENGTH: 21
<212> TYPE: PRT
<213> ORGANISM: Homo sapiens

<400> SEQUENCE: 128

Leu Pro Asp Ser Pro Val Gly Gln Leu His Ala Ser Leu Leu Gly Leu
1               5                   10                  15

Ser Gln Leu Leu Gln
            20

<210> SEQ ID NO 129
```

```
<211> LENGTH: 20
<212> TYPE: PRT
<213> ORGANISM: Homo sapiens

<400> SEQUENCE: 129

Gln Cys Gln Gln Leu Ser Gln Lys Leu Cys Thr Leu Ala Trp Ser Ala
1               5                   10                  15

His Pro Leu Val
            20

<210> SEQ ID NO 130
<211> LENGTH: 14
<212> TYPE: PRT
<213> ORGANISM: Homo sapiens

<400> SEQUENCE: 130

Gly His Met Asp Leu Arg Glu Glu Gly Asp Glu Thr Thr
1               5                   10

<210> SEQ ID NO 131
<211> LENGTH: 19
<212> TYPE: PRT
<213> ORGANISM: Homo sapiens

<400> SEQUENCE: 131

Leu Leu Pro Asp Ser Pro Val Gly Gln Leu His Ala Ser Leu Leu Gly
1               5                   10                  15

Leu Ser Gln

<210> SEQ ID NO 132
<211> LENGTH: 20
<212> TYPE: PRT
<213> ORGANISM: Homo sapiens

<400> SEQUENCE: 132

Leu Leu Arg Phe Lys Ile Leu Arg Ser Leu Gln Ala Phe Val Ala Val
1               5                   10                  15

Ala Ala Arg Val
            20

<210> SEQ ID NO 133
<211> LENGTH: 31
<212> TYPE: PRT
<213> ORGANISM: Homo sapiens

<400> SEQUENCE: 133

Leu Leu Leu His Lys Lys Glu Asp Gly Ile Trp Ser Thr Asp Ile Leu
1               5                   10                  15

Lys Asp Gln Lys Glu Pro Lys Asn Lys Thr Phe Leu Arg Cys Glu
            20                  25                  30

<210> SEQ ID NO 134
<211> LENGTH: 11
<212> TYPE: PRT
<213> ORGANISM: Homo sapiens

<400> SEQUENCE: 134

Lys Ser Ser Arg Gly Ser Ser Asp Pro Gln Gly
1               5                   10

<210> SEQ ID NO 135
<211> LENGTH: 19
<212> TYPE: PRT
```

```
<213> ORGANISM: Mus musculus

<400> SEQUENCE: 135

Pro Glu Glu Asp Asp Ile Thr Trp Thr Ser Asp Gln Arg His Gly Val
1               5                   10                  15

Ile Gly Ser

<210> SEQ ID NO 136
<211> LENGTH: 18
<212> TYPE: PRT
<213> ORGANISM: Mus musculus

<400> SEQUENCE: 136

Pro Asp Ser Arg Ala Val Thr Cys Gly Met Ala Ser Leu Ser Ala Glu
1               5                   10                  15

Lys Val

<210> SEQ ID NO 137
<211> LENGTH: 9
<212> TYPE: PRT
<213> ORGANISM: Mus musculus

<400> SEQUENCE: 137

Thr Pro Asp Ala Pro Gly Glu Thr Val
1               5

<210> SEQ ID NO 138
<211> LENGTH: 20
<212> TYPE: PRT
<213> ORGANISM: Mus musculus

<400> SEQUENCE: 138

Asp Ser Asp Ile Phe Lys Gly Glu Pro Ala Leu Leu Pro Asp Ser Pro
1               5                   10                  15

Met Glu Gln Leu
            20

<210> SEQ ID NO 139
<211> LENGTH: 20
<212> TYPE: PRT
<213> ORGANISM: Mus musculus

<400> SEQUENCE: 139

Thr Gln Gln Met Pro Ser Leu Ser Ser Gln Gln Trp Gln Arg Pro
1               5                   10                  15

Leu Leu Arg Ser
            20

<210> SEQ ID NO 140
<211> LENGTH: 65
<212> TYPE: PRT
<213> ORGANISM: Artificial Sequence
<220> FEATURE:
<223> OTHER INFORMATION: Synthetic Peptide

<400> SEQUENCE: 140

Gly Ser Gly Ser Gly Ser Gly Leu His Ala Ser Leu Leu Gly Leu Ser
1               5                   10                  15

Gln Leu Leu Gln Pro Glu Gly His His Trp Glu Thr Gln Gln Ile Pro
            20                  25                  30

Ser Leu Ser Pro Ser Gln Pro Trp Gln Arg Leu Leu Leu Arg Phe Lys
        35                  40                  45
```

```
Ile Leu Arg Ser Leu Gln Ala Phe Val Ala Gly Ser Gly Ser Gly Ser
        50                  55                  60

Gly
65

<210> SEQ ID NO 141
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 141

His Ala Ser Leu Leu Gly Leu Ser Gln Leu Leu Gln Pro Glu Gly His
1               5                   10                  15

His Trp Glu Thr Gln Gln Ile Pro Ser Leu Ser Pro Ser Gln Pro Trp
                20                  25                  30

Gln Arg Leu Leu Leu Arg Phe Lys Ile Leu Arg Ser Leu Gln Ala Phe
            35                  40                  45

Ala Val Ala Ala Arg Val
        50
```